(12) United States Patent
Maliga et al.

(10) Patent No.: US 6,624,296 B1
(45) Date of Patent: Sep. 23, 2003

(54) PLASTID PROMOTERS FOR TRANSGENE EXPRESSION IN THE PLASTIDS OF HIGHER PLANTS

(75) Inventors: Pal Maliga, East Brunswick, NJ (US); Daniel Silhavy, Budapest (HU); Priya Sriraman, Piscataway, NJ (US)

(73) Assignee: Rutgers, The State University of New Jersey, East Brunswick, NJ (US)

( * ) Notice: Subject to any disclaimer, the term of this patent is extended or adjusted under 35 U.S.C. 154(b) by 0 days.

(21) Appl. No.: 09/445,283

(22) PCT Filed: Jun. 3, 1998

(86) PCT No.: PCT/US98/11437
§ 371 (c)(1),
(2), (4) Date: Dec. 3, 1999

(87) PCT Pub. No.: WO98/55595
PCT Pub. Date: Dec. 10, 1998

Related U.S. Application Data

(60) Provisional application No. 60/048,376, filed on Jun. 3, 1997, and provisional application No. 60/058,670, filed on Sep. 12, 1997.

(51) Int. Cl.$^7$ .................. C12N 15/29; C12N 15/82; C12N 5/04; C12N 5/10
(52) U.S. Cl. .................. 536/24.1; 800/287; 435/419
(58) Field of Search .................. 536/24.1; 800/287; 435/419

(56) References Cited

U.S. PATENT DOCUMENTS 5,877,402 A    3/1999   Maliga et al.

FOREIGN PATENT DOCUMENTS

EP           0 251 654 A2    6/1987

OTHER PUBLICATIONS

Liere et al, 1999, EMBO J. 18:249–257.*
Clarke, A. K. et al. Identification and expression of the chloroplast clpP gene in the conifer *Pinus contorta* Plant Molecular Biology 26:851–862 Nov. 1994 No. 3 1994.*
Donald et al. Mutation of either G box or I box sequences profoundly affects expression from the arabidopsis rbcS–1A promoter EMBO journal vol. 9 No. 6pp. 1717–1726 1990.*
Maier et al. Complete sequence of the maize chloroplast genome:gene content, hotspots of divergence and fine tuning of genetic information by transcript editing J. Mol. Biol. 1995 251, 614–628.*
zma86563 140384 bp DNA circular PLN Apr. 12, 2001.*
Gray, J. C. et al., "Nucleotide sequence of a wheat chloroplast gene encoding the proteolytic subunit of an ATP–dependent protease." 1990, Plant Molecular Biology, vol. 15, pp. 947–950.*

Gabor L. Igloi, et al. Nucleotide sequence of the maize chloroplast rpo B/$C_1$/$C_2$ operon: Comparison between the derived protein primary structures from various organisms with respect to functional domains—Mol Gen Genet (1990) 221:379–394.

Wilhelm Gruissem, et al., Analysis of promoter regions for the spinach chloroplast rbcL, atpB and psbA genes—The EMBO Journal vol. (1985) 4, No. 13A, 3375–3383.

Christopher D. Rock, et al. The maize plastic psbB–psbF––petB–petD gene cluster: spliced and unspliced petB and petD RNAs encode alternative products—Curr Genet (1987) 12:69–77.

Zs. Schwarz, et al. The primary structure of 16S rDNA from *Zea mays* chloroplast is homologous to *E. coli* 16S rRNA— Nature vol. 283 Feb. 21, 1980.

Alan D. Blowers, et al. Transcriptional Analysis of Endogenous and Foreign Genes in Chloroplast Transformants of Chlamydomonas—The Plant Cell (Nov. 1990) 2, 1059–1070.

Guang–Ning Ye, et al. Optimization of delivery of foreign DNA into higher–plant chloroplasts—Plant Molecular Biology (1990) 15:809–819.

Jeffrey M. Staub, et al. Accumulation of D1 polypeptide in tobacco plastids is regulated via the untranslated region of the psbA and mRNA—The EMBO Journal (1993) vol. 12, No. 2, 601–606.

Adrian K. Clarke, et al. Identification and expression of the chloroplast clpP gene in the conifer *Pinus contorta*—Plant Molecular Biology (1994) 26: 851–862.

J.C. Gray, et al. Nucleotide sequence of a wheat chloroplast gene encoding the proteolytic subunit of an ATP–dependent protease—Plant Molecular Biology (1990)15:947–950.

Eric Sun, et al. In Vitro Analysis of the Pea Chloroplast 16S rRNA Gene Promoter—(Dec. 1989) vol. 9, No. 12, 5650–5659.

H. Daniell, et al. Transient Expression of β–glucuronidase in different cellular compartments following biolistic delivery of foreign DNA into wheat leaves and calli.—Plant Cell Reports (1991) 9:615–619.

* cited by examiner

*Primary Examiner*—David T. Fox
(74) *Attorney, Agent, or Firm*—Dann Dorfman Herrell & Skillman, P.C.

(57) ABSTRACT

The present invention provides promoter elements useful for stably transforming the plastids of higher plants. The constructs described herein contain unique promoters that are transcribed by both nuclear encoded plastid RNA polymerases, plastid encoded plastid RNA polymerases or both. Use of the novel constructs of the invention facilitates transformation of a wider range of plant species and enables ubiquitous expression of a transforming DNA in plastids of multicellular plants.

3 Claims, 18 Drawing Sheets

Fig. 4A
Fig. 4B
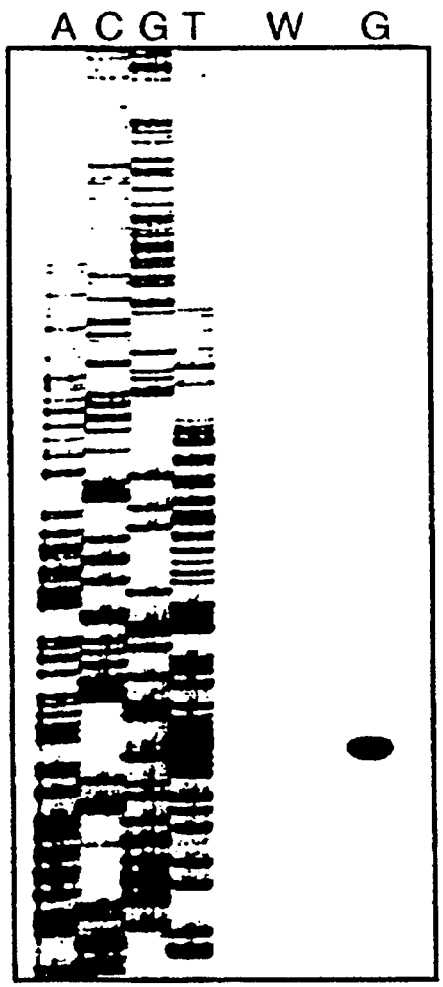
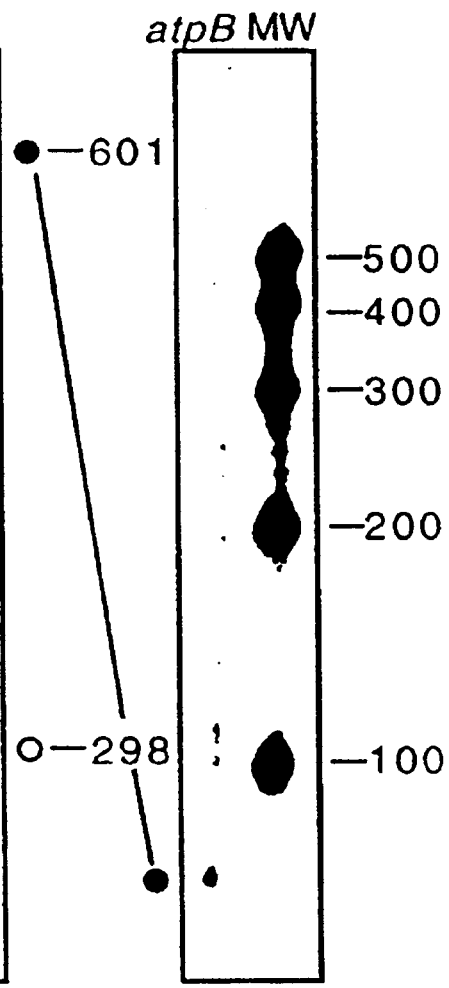
Fig. 4C
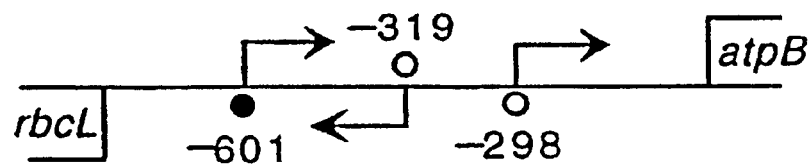

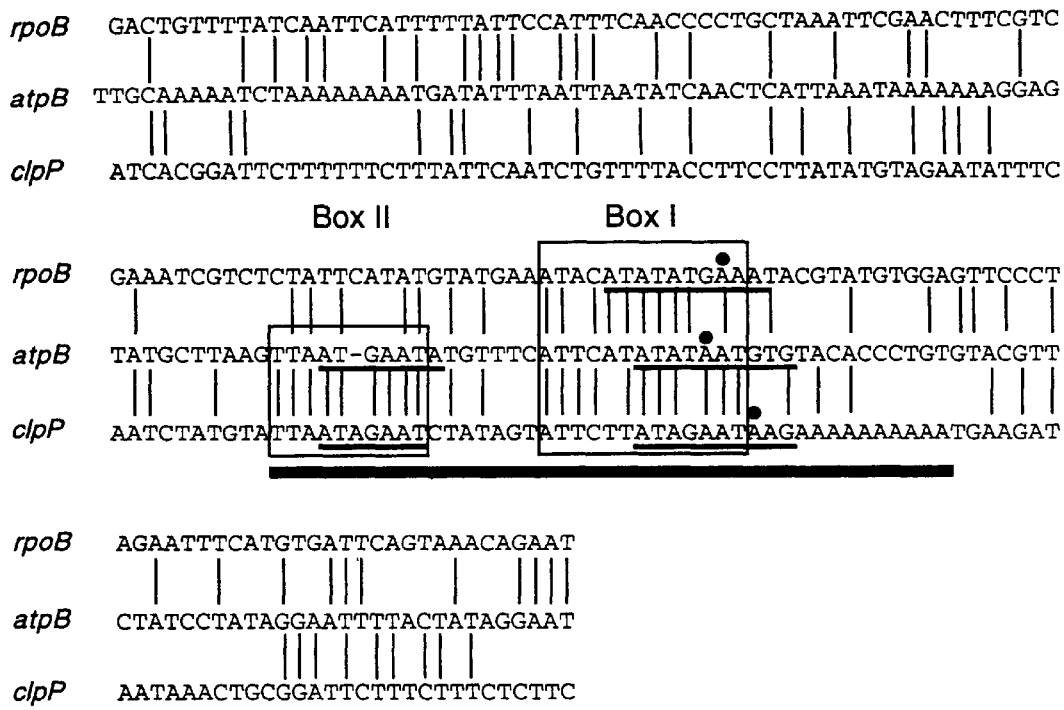

Figure 6.

```
Seq.
ID
#18  Marchantia    TAAATAAATAGAATTTCATTTTTACGTTTTTTTATTATAG
#19  Pinus         TGTTACACAACTTCATATACTTTACGTTCCCATATTATAG
#20  Spinach       TAAAGACAATAACCGTAATTATTACGTTTCCACATCAAAG
#21  Tobacco       TAAAGACAATAAAAAAAATTGTTACGTTTCCACCTCAAAG
#22  Rice          TTCTTTCTTTCTCTTCCATTCTTACGTTTCCATATTAAAG
#23  Maize         TTCTTTCTTTCTCTTCCATTCTTACGTTTCCATATTAAAG
24  Arabidopsis   TTAAAAAACGAAACCCCAATTTTTACGTTTCCACATCAAAG Marchantia    AAGAGTATT-TTGTTTG--TGGAAGAAAAAAAAATGCCT
     Pinus         TATAGTGCT-TAACTTC--TTTCCATTAAAACAAATGCCC
     Spinach       TGAATAGAGTACTTAATTTTTTTCTTTCATTTAATGCCT
     Tobacco       TGAATATAGTA-TTTAGTTCTTTCTTTCATTTAATGCCT
     Rice          TGTAGTTTTCTTACTTA--AATTTAATAATATTAATCTAATATG
     Maize         TGTAGTTTTTTTACTTA--AATTTAATAATATTAATCTAATATG
     Arabidopsis   TGAATAGAGAACTTCATTCTCTTTTTTTTTCATTTCATGCCT
```

FIG. 9

```
         SacI  .74579 (c)
   1     gagctcTATA AAGACAATAA AAAAAATTGT TACGTTTCCA CCTCAAAGTG
           .74533 (c)
  51     AAActcgaga attcagttgt agggagggat ccATGGAACA AAAACTCATT
 101     TCTGAAGAAG ACTTGgtacg tcctgtagaa accccaaccc gtgaaatcaa
 151     aaaactcgac ggcctgtggg cattcagtct ggatcgcgaa aactgtggaa
 201     ttgatcagcg ttggtgggaa agcgcgttac aagaaagccg ggcaattgct
 251     gtgccaggca gttttaacga tcagttcgcc gatgcagata ttcgtaatta
 301     tgcgggcaac gtctggtatc agcgcgaagt ctttataccg aaaggttggg
 351     caggccagcg tatcgtgctg cgtttcgatg cggtcactca ttacggcaaa
 401     gtgtgggtca ataatcagga agtgatggag catcagggcg gctatacgcc
 451     atttgaagcc gatgtcacgc cgtatgttat tgccgggaaa agtgtacgta
 501     tcaccgtttg tgtgaacaac gaactgaact ggcagactat cccgccggga
 551     atggtgatta ccgacgaaaa cggcaagaaa aagcagtctt acttccatga
 601     tttctttaac tatgccggaa tccatcgcag cgtaatgctc tacaccacgc
 651     cgaacacctg ggtggacgat atcaccgtgg tgacgcatgt cgcgcaagac
 701     tgtaaccacg cgtctgttga ctggcaggtg gtggccaatg gtgatgtcag
 751     cgttgaactg cgtgatgcgg atcaacaggt ggttgcaact ggacaaggca
 801     ctagcgggac tttgcaagtg gtgaatccgc acctctggca accgggtgaa
 851     ggttatctct atgaactgtg cgtcacagcc aaaagccaga cagagtgtga
 901     tatctacccg cttcgcgtcg gcatccggtc agtggcagtg aagggccaac
 951     agttcctgat taaccacaaa ccgttctact ttactggctt tggtcgtcat
1001     gaagatgcgg acttacgtgg caaaggattc gataacgtgc tgatggtgca
```

FIG. 13A

| | | | | |
|---|---|---|---|---|
| 1051 | cgaccacgca | ttaatggact | ggattggggc | caactcctac | cgtacctcgc |
| 1101 | attaccctta | cgctgaagag | atgctcgact | gggcagatga | acatggcatc |
| 1151 | gtggtgattg | atgaaactgc | tgctgtcggc | tttaacctct | ctttaggcat |
| 1201 | tggtttcgaa | gcgggcaaca | agccgaaaga | actgtacagc | gaagaggcag |
| 1251 | tcaacgggga | aactcagcaa | gcgcacttac | aggcgattaa | agagctgata |
| 1301 | gcgcgtgaca | aaaccaccc | aagcgtggtg | atgtggagta | ttgccaacga |
| 1351 | accggatacc | cgtccgcaag | tgcacgggaa | tatttcgcca | ctggcggaag |
| 1401 | caacgcgtaa | actcgacccg | acgcgtccga | tcacctgcgt | caatgtaatg |
| 1451 | ttctgcgacg | ctcacaccga | taccatcagc | gatctctttg | atgtgctgtg |
| 1501 | cctgaaccgt | tattacggat | ggtatgtcca | aagcggcgat | ttggaaacgg |
| 1551 | cagagaaggt | actggaaaaa | gaacttctgg | cctggcagga | gaaactgcat |
| 1601 | cagccgatta | tcatcaccga | atacggcgtg | gatacgttag | ccgggctgca |
| 1651 | ctcaatgtac | accgacatgt | ggagtgaaga | gtatcagtgt | gcatggctgg |
| 1701 | atatgtatca | ccgcgtcttt | gatcgcgtca | gcgccgtcgt | cggtgaacag |
| 1751 | gtatggaatt | cgccgattt | tgcgacctcg | caaggcatat | tgcgcgttgg |
| 1801 | cggtaacaag | aaagggatct | tcactcgcga | ccgcaaaccg | aagtcggcgg |
| 1851 | cttttctgct | gcaaaaacgc | tggactggca | tgaacttcgg | tgaaaaaccg |
| 1901 | cagcagggag | gcaaacaatg | aatcaacaac | tctcctggcg | caccatcgtc |
| | | | | ▪5087 (c) | |
| 1951 | ggctacagcc | tcggtgggga | attgctctag | aGAAATTCAA | TTAAGGAAAT |
| 2001 | AAATTAAGGA | AATACAAAAA | GGGGGGTAGT | CATTTGTATA | TAACTTTGTA |
| 2051 | TGACTTTTCT | CTTCTATTTT | TTTGTATTTC | CTCCCTTTCC | TTTTCTATTT |
| | | | | ▪4939 (c) | |
| 2101 | GTATTTTTTT | ATCATTGCTT | CCATTGAATT | aattcaagct | t HindIII |

FIG. 13B

*16SrDNA*

```
maize  CACCACGATCGAACGGGAATGGATAGGAGGCTTGTGGGATTGACGTGATA
rice   CGCCACGATCGAACGGGAATGGATAAGAGGCTTGTGGGATTGACGTGATA
                         -1170
maize  GGGTAGGGTTGGCTATACTGCTGGTGGCGAACTCCAGGCTAATAATCTGA
rice   GGGTAGGGTTGGCTATACTGCTGGTGGCGAACTCCAGGCTAATAATCTGA
                         -1160
maize  AGCGCATGGATACAAGTTATCCTTGGAAGGAAAGACAATTCCGAATCCGC
rice   AGCGCATGGATACAAGTTATCCTTGGAAGGAAAGACAATTCCGAATCCGC
                 -30                                    5'
maize  TTTGTCTACGAATAAGGAAGCTATAAGTAATGCAACTATGAATCTCATGG
rice   TTTGTCTACGAATAAGGAAGCTATAAGTAATGCAACTATGAATCTCATGG
                 -28
```

FIG. 17A

*clpP*

```
              -111
maize  TATAGTATTCTTATAGAATAAGAAAAAAAAAATGAAGATAATAAACTGCG
rice   TATAGTATTCTTATAGAATAAGAAAAAAAA-CGTGAAAACAATAAACTGCG
              -111
```

FIG. 17B

SEQUENCE LISTING

<160> NUMBER OF SEQ ID NOS: 64

<210> SEQ ID NO 1
<211> LENGTH: 149
<212> TYPE: DNA
<213> ORGANISM: Zea mays

<400> SEQUENCE: 1

```
gactgtttta tcaattcatt tttattccat ttcaacccct gctaaattcg aactttcgtc      60
gaaatcgtct ctattcatat gtatgaaata catatatgaa atacgtatgt ggagttccct     120
agaatttcat gtgattcagt aaacagaat                                       149
```

<210> SEQ ID NO 2
<211> LENGTH: 149
<212> TYPE: DNA
<213> ORGANISM: Zea mays

<400> SEQUENCE: 2

```
ttgcaaaaat ctaaaaaaaa tgatatttaa ttaatatcaa ctcattaaat aaaaaaagga      60
gtatgcttaa gttaatgaat atgtttcatt catatataat gtgtacaccc tgtgtacgtt     120
ctatcctata ggaatttac tataggaat                                        149
```

<210> SEQ ID NO 3
<211> LENGTH: 149
<212> TYPE: DNA
<213> ORGANISM: Zea mays

```
<400> SEQUENCE: 3
atcacggatt cttttttctt tattcaatct gttttacctt ccttatatgt agaatatttc      60
aatctatgta ttaatagaat ctatagtatt cttatagaat aagaaaaaaa aaatgaagat     120
aataaactgc ggattctttc tttctcttc                                      149

<210> SEQ ID NO 4
<211> LENGTH: 41
<212> TYPE: DNA
<213> ORGANISM: Zea mays

<400> SEQUENCE: 4
taagttaatg aatatgtttc attcatatat aatgtgacac c                         41

<210> SEQ ID NO 5
<211> LENGTH: 41
<212> TYPE: DNA
<213> ORGANISM: Sorghum

<400> SEQUENCE: 5
taagttaatg aatatgtttc attcatatat aatgtgacac c                         41

<210> SEQ ID NO 6
<211> LENGTH: 41
<212> TYPE: DNA
<213> ORGANISM: Hordeum vulgare

<400> SEQUENCE: 6
taggttaatg aatatgtttc attcatatat aatgcgacac c                         41

<210> SEQ ID NO 7
<211> LENGTH: 41
<212> TYPE: DNA
<213> ORGANISM: Triticum aestivum

<400> SEQUENCE: 7
taggttaatg aatatgtttc attcatatat aatgcgacac c                         41

<210> SEQ ID NO 8
<211> LENGTH: 41
<212> TYPE: DNA
<213> ORGANISM: Oryza sativa

<400> SEQUENCE: 8
tcattcatat aatatgtttc attcatatat aatgggacac c                         41

<210> SEQ ID NO 9
<211> LENGTH: 41
<212> TYPE: DNA
<213> ORGANISM: Zea mays

<400> SEQUENCE: 9
ctctattcat atgtatgaaa tacatatatg aaatacgtat g                         41

<210> SEQ ID NO 10
<211> LENGTH: 41
<212> TYPE: DNA
<213> ORGANISM: Oryza sativa

<400> SEQUENCE: 10
ctctattcat atgtatgaaa tacatatatg aaatacgtat g                         41
```

```
<210> SEQ ID NO 11
<211> LENGTH: 39
<212> TYPE: DNA
<213> ORGANISM: Nicotinium tobacco

<400> SEQUENCE: 11
caggttggaa tgtgtattat cataataatg gtagaaatg                              39

<210> SEQ ID NO 12
<211> LENGTH: 41
<212> TYPE: DNA
<213> ORGANISM: Zea mays

<400> SEQUENCE: 12
ttaatagaat ctatagtatt cttatagaat aagaaaaaaa a                           41

<210> SEQ ID NO 13
<211> LENGTH: 41
<212> TYPE: DNA
<213> ORGANISM: Oryza sativa

<400> SEQUENCE: 13
ttaatagaat ctatagtatt catatagaat aagaaaaaaa c                           41

<210> SEQ ID NO 14
<211> LENGTH: 41
<212> TYPE: DNA
<213> ORGANISM: Triticum aestivum

<400> SEQUENCE: 14
ttaatagaat ctatagtatt catatagaat aagaataaaa t                           41

<210> SEQ ID NO 15
<211> LENGTH: 251
<212> TYPE: DNA
<213> ORGANISM: Nicotinium tobacco

<400> SEQUENCE: 15
tcgaatcacc attcttttt ctttattcaa tctgtcttat cctacttata tgtataatct        60
ttcaatctat gtattatttc aatctacgta cttaatagaa tctatagtat tcatatagaa      120
taagaaaaaa acgtgaaaac aataaactgc ggattctttc tttctcttcc attcttacgt      180
ttccatatta agtgtagtt ttcttactta aatttaataa tattaatcta atatgcccat       240
tggtgttcca a                                                           251

<210> SEQ ID NO 16
<211> LENGTH: 199
<212> TYPE: DNA
<213> ORGANISM: Oryza sativa

<400> SEQUENCE: 16
tagaaagacc tattcgtaat aatttgagtt tattcattct gtctttcttt atgaattttt       60
ataatctatg gataaaataa atacgataaa aaccaatatg aatattataa agacaataaa      120
aaaaattgtt acgttccac ctcaaagtga aatatagtat ttagttcttt ctttcatttta      180 atgcctattg gtgttccaa                                                   199

<210> SEQ ID NO 17
<211> LENGTH: 283
<212> TYPE: DNA
<213> ORGANISM: Oryza sativa
```

-continued

<400> SEQUENCE: 17
gagctcgaat caccattctt ttttctttat tcaatctgtc ttatcctact tatatgtata    60
atctttcaat ctatgtatta tttcaatcta cgtacttaat agaatctata gtattcatat   120
agaataagaa aaaaacgtga aaacaataaa ctgcggattc tttctttctc ttccattctt   180
acgtttccat attaaagtgt agttttctta cttaaattta ataatattaa tctaaatatgc  240 ccattggtgt tccaagaatt cagttgtagg gagggatcca tgg                     283

<210> SEQ ID NO 18
<211> LENGTH: 77
<212> TYPE: DNA
<213> ORGANISM: Marchantia polymorpha

<400> SEQUENCE: 18
taaataaata gaatttcatt tttacgtttt tttattatag aagagtattt tgtttgtgga    60
agaaaaaaaa aatgcct                                                   77

<210> SEQ ID NO 19
<211> LENGTH: 77
<212> TYPE: DNA
<213> ORGANISM: Pinus contorta

<400> SEQUENCE: 19
tgttacacaa cttcatatac tttacgttcc catattatag tatagtgctt aacttctttc    60
cattaaaaca aatgccc                                                   77

<210> SEQ ID NO 20
<211> LENGTH: 80
<212> TYPE: DNA
<213> ORGANISM: Spinacia oleracea

<400> SEQUENCE: 20
taaagacaat aaccgtaatt attacgtttc cacatcaaag tgaaatagag tacttaattt    60
ttttctttca tttaatgcct                                                80

<210> SEQ ID NO 21
<211> LENGTH: 79
<212> TYPE: DNA
<213> ORGANISM: Nicotinium tobacco

<400> SEQUENCE: 21
taaagacaat aaaaaaaatt gttacgtttc cacctcaaag tgaaatatag tatttagttc    60
tttctttcat ttaatgcct                                                 79

<210> SEQ ID NO 22
<211> LENGTH: 82
<212> TYPE: DNA
<213> ORGANISM: Oryza sativa

<400> SEQUENCE: 22
ttctttcttt ctcttccatt cttacgtttc catattaaag tgtagttttc ttacttaaat    60
ttaataatat taatctaata tg                                             82

<210> SEQ ID NO 23
<211> LENGTH: 82
<212> TYPE: DNA
<213> ORGANISM: Zea mays

-continued

<400> SEQUENCE: 23
ttctttcttt ctcttccatt cttacgtttc catattaaag tgtagttttt ttacttaaat    60
ttaataatat taatctaata tg    82

<210> SEQ ID NO 24
<211> LENGTH: 83
<212> TYPE: DNA
<213> ORGANISM: Arabidopsis

<400> SEQUENCE: 24
ttaaaaaacg aaaccccaat tttacgtttc cacatcaaag tgaaatagag aacttcattc    60 tcttttttt tcatttcatg cct    83

<210> SEQ ID NO 25
<211> LENGTH: 59
<212> TYPE: DNA
<213> ORGANISM: Nicotinium tobacco

<400> SEQUENCE: 25
gagctctata aagacaataa aaaaaattgt tacgtttcca cctcaaagtg aaactcgag     59

<210> SEQ ID NO 26
<211> LENGTH: 35
<212> TYPE: DNA
<213> ORGANISM: Nicotinium tobacco

<400> SEQUENCE: 26
aaaaaaaatt gttacgtttc cacctcaaag tgaaa    35

<210> SEQ ID NO 27
<211> LENGTH: 2141
<212> TYPE: DNA
<213> ORGANISM: Artificial Sequence
<220> FEATURE:
<223> OTHER INFORMATION: Chimeric uidA gene

<400> SEQUENCE: 27
gagctctata aagacaataa aaaaaattgt tacgtttcca cctcaaagtg aaactcgaga    60
attcagttgt agggagggat ccatggaaca aaaactcatt tctgaagaag acttggtacg   120
tcctgtagaa accccaaccc gtgaaatcaa aaaactcgac ggcctgtggg cattcagtct   180
ggatcgcgaa aactgtggaa ttgatcagcg ttggtgggaa agcgcgttac aagaaagccg   240
ggcaattgct gtgccaggca gttttaacga tcagttcgcc gatgcagata ttcgtaatta   300
tgcgggcaac gtctggtatc agcgcgaagt ctttataccg aaaggttggg caggccagcg   360
tatcgtgctg cgtttcgatg cggtcactca ttacggcaaa gtgtgggtca ataatcagga   420
agtgatggag catcagggcg gctatacgcc atttgaagcc gatgtcacgc cgtatgttat   480
tgccgggaaa agtgtacgta tcaccgtttg tgtgaacaac gaactgaact ggcagactat   540
cccgccggga atggtgatta ccgacgaaaa cggcaagaaa aagcagtctt acttccatga   600
tttctttaac tatgccggaa tccatcgcag cgtaatgctc tacaccacgc cgaacacctg   660
ggtggacgat atcaccgtgg tgacgcatgt cgcgcaagac tgtaaccacg cgtctgttga   720
ctggcaggtg gtggccaatg gtgatgtcag cgttgaactg cgtgatgcgg atcaacaggt   780
ggttgcaact ggacaaggca ctagcgggac tttgcaagtg gtgaatccgc acctctggca   840
accgggtgaa ggttatctct atgaactgtg cgtcacagca aaaagccaga cagagtgtga   900
tatctacccg cttcgcgtcg gcatccggtc agtggcagtg aagggccaac agttcctgat   960

```
taaccacaaa ccgttctact ttactggctt tggtcgtcat gaagatgcgg acttacgtgg   1020
caaaggattc gataacgtgc tgatggtgca cgaccacgca ttaatggact ggattggggc   1080
caactcctac cgtacctcgc attacccttc cgctgaagag atgctcgact gggcagatga   1140
acatggcatc gtggtgattg atgaaactgc tgctgtcggc tttaacctct ctttaggcat   1200
tggtttcgaa gcgggcaaca agccgaaaga actgtacagc gaagaggcag tcaacgggga   1260
aactcagcaa gcgcacttac aggcgattaa agagctgata gcgcgtgaca aaaaccaccc   1320
aagcgtggtg atgtggagta ttgccaacga accggatacc cgtccgcaag tgcacgggaa   1380
tatttcgcca ctggcggaag caacgcgtaa actcgacccg acgcgtccga tcacctgcgt   1440
caatgtaatg ttctgcgacg ctcacaccga taccatcagc gatctctttg atgtgctgtg   1500
cctgaaccgt tattacggat ggtatgtcca agcggcgat ttggaaacgg cagagaaggt   1560
actggaaaaa gaacttctgg cctggcagga gaaactgcat cagccgatta tcatcaccga   1620
atacggcgtg gatacgttag ccgggctgca ctcaatgtac accgacatgt ggagtgaaga   1680
gtatcagtgt gcatggctgg atatgtatca ccgcgtcttt gatcgcgtca cgccgtcgt   1740 cggtgaacag gtatggaatt cgccgatttt tgcgacctcg caaggcatat tgcgcgttgg   1800
cggtaacaag aaagggatct tcactcgcga ccgcaaaccg aagtcggcgg cttttctgct   1860
gcaaaaacgc tggactggca tgaacttcgg tgaaaaaccg cagcagggag gcaaacaatg   1920
aatcaacaac tctcctggcg caccatcgtc ggctacagcc tcggtgggga attgctctag   1980
agaaattcaa ttaaggaaat aaattaagga aatacaaaaa gggggggtagt catttgtata   2040 taactttgta tgactttcct cttctatttt tttgtatttc ctccctttcc ttttctattt   2100
gtattttttt atcattgctt ccattgaatt aattcaagct t                      2141

<210> SEQ ID NO 28
<211> LENGTH: 200
<212> TYPE: DNA
<213> ORGANISM: Zea mays

<400> SEQUENCE: 28
caccacgatc gaacgggaat ggataggagg cttgtgggat tgacgtgata gggtagggtt     60
ggctatactg ctggtggcga actccaggct aataatctga agcgcatgga tacaagttat    120
ccttggaagg aaagacaatt ccgaatccgc tttgtctacg aataaggaag ctataagtaa    180
tgcaactatg aatctcatgg                                                200

<210> SEQ ID NO 29
<211> LENGTH: 200
<212> TYPE: DNA
<213> ORGANISM: Oryza sativa

<400> SEQUENCE: 29
cgccacgatc gaacgggaat ggataagagg cttgtgggat tgacgtgata gggtagggtt     60
ggctatactg ctggtggcga actccaggct aataatctga agcgcatgga tacaagttat    120
ccttggaagg aaagacaatt ccgaatccgc tttgtctacg aataaggaag ctataagtaa    180
tgcaactatg aatctcatgg                                                200

<210> SEQ ID NO 30
<211> LENGTH: 61
<212> TYPE: DNA
<213> ORGANISM: Zea mays
```

<400> SEQUENCE: 30
ttaatagaat ctatagtatt cttatagaat aagaaaaaaa aaatgaagat aataaactgc    60
g                                                                   61

<210> SEQ ID NO 31
<211> LENGTH: 60
<212> TYPE: DNA
<213> ORGANISM: Oryza sativa

<400> SEQUENCE: 31
ttaatagaat ctatagtatt catatagaat aagaaaaaaa cgtgaaaaca ataaactgcg    60

<210> SEQ ID NO 32
<211> LENGTH: 133
<212> TYPE: DNA
<213> ORGANISM: Artificial Sequence
<220> FEATURE:
<223> OTHER INFORMATION: Prrn promoter

<400> SEQUENCE: 32
gctcccccgc cgtcgttcaa tgagaatgga taagaggctc gtgggattga cgtgagggggg    60 cagggatggc tatattctgg gagcgaactc cgggcgaata cgaagcgctt ggatacagtt   120
gtagggaggg att                                                      133

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33
gagaggaatg gaagtgattg aca                                           23

<210> SEQ ID NO 34
<211> LENGTH: 19
<212> TYPE: DNA
<213> ORGANISM: Artificial Sequence
<220> FEATURE:
<223> OTHER INFORMATION: Primer

<400> SEQUENCE: 34
gagcagggtc ggtcaaatc                                                19

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
atcctagcgt gagggaatgc ta                                            22

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
aggtctgatg gtatatctca gtat                                          24

<210> SEQ ID NO 37
<211> LENGTH: 15
<212> TYPE: DNA
<213> ORGANISM: Artificial Sequence
<220> FEATURE:
<223> OTHER INFORMATION: Primer

<400> SEQUENCE: 37
cgcttctgta actgg                                                    15

<210> SEQ ID NO 38
<211> LENGTH: 16
<212> TYPE: DNA
<213> ORGANISM: Artificial Sequence
<220> FEATURE:
<223> OTHER INFORMATION: Primer

<400> SEQUENCE: 38
tgactgtcaa ctacag                                                   16

<210> SEQ ID NO 39
<211> LENGTH: 26
<212> TYPE: DNA
<213> ORGANISM: Artificial Sequence
<220> FEATURE:
<223> OTHER INFORMATION: Primer

<400> SEQUENCE: 39
ggtacttttg gaaccaat gggcat                                          26

<210> SEQ ID NO 40
<211> LENGTH: 26
<212> TYPE: DNA
<213> ORGANISM: Artificial Sequence
<220> FEATURE:
<223> OTHER INFORMATION: Primer

<400> SEQUENCE: 40
gaagtagtag gattggttct cataat                                        26

<210> SEQ ID NO 41
<211> LENGTH: 27
<212> TYPE: DNA
<213> ORGANISM: Artificial Sequence
<220> FEATURE:
<223> OTHER INFORMATION: Primer

<400> SEQUENCE: 41
ggtctagaat tcctatcgaa ttccttc                                       27

<210> SEQ ID NO 42
<211> LENGTH: 24
<212> TYPE: DNA
<213> ORGANISM: Artificial Sequence
<220> FEATURE:
<223> OTHER INFORMATION: Primer

<400> SEQUENCE: 42
gaatctacaa aatccctcga attg                                          24

<210> SEQ ID NO 43
<211> LENGTH: 20
<212> TYPE: DNA
<213> ORGANISM: Artificial Sequence
<220> FEATURE:

-continued

<223> OTHER INFORMATION: Primer

<400> SEQUENCE: 43
actcttcatc aatccctacg                                           20

<210> SEQ ID NO 44
<211> LENGTH: 25
<212> TYPE: DNA
<213> ORGANISM: Artificial Sequence
<220> FEATURE:
<223> OTHER INFORMATION: Primer

<400> SEQUENCE: 44
ggtctagact acactttaat atgga                                     25

<210> SEQ ID NO 45
<211> LENGTH: 22
<212> TYPE: DNA
<213> ORGANISM: Artificial Sequence
<220> FEATURE:
<223> OTHER INFORMATION: Primer

<400> SEQUENCE: 45
gggaattctg tttgtaagaa ga                                        22

<210> SEQ ID NO 46
<211> LENGTH: 29
<212> TYPE: DNA
<213> ORGANISM: Artificial Sequence
<220> FEATURE:
<223> OTHER INFORMATION: Primer

<400> SEQUENCE: 46
ggctcgaggg acaactcgat aggattagg                                 29

<210> SEQ ID NO 47
<211> LENGTH: 27
<212> TYPE: DNA
<213> ORGANISM: Artificial Sequence
<220> FEATURE:
<223> OTHER INFORMATION: Primer

<400> SEQUENCE: 47
ggtctagaat ctagcaatca tggaatc                                   27

<210> SEQ ID NO 48
<211> LENGTH: 26
<212> TYPE: DNA
<213> ORGANISM: Artificial Sequence
<220> FEATURE:
<223> OTHER INFORMATION: Primer

<400> SEQUENCE: 48
ggctcgagcg tgctattcta aatcgt                                    26

<210> SEQ ID NO 49
<211> LENGTH: 23
<212> TYPE: DNA
<213> ORGANISM: Artificial Sequence
<220> FEATURE:
<223> OTHER INFORMATION: Primer

<400> SEQUENCE: 49
gggagctcga atcaccattc ttt                                       23

```
<210> SEQ ID NO 50
<211> LENGTH: 27
<212> TYPE: DNA
<213> ORGANISM: Artificial Sequence
<220> FEATURE:
<223> OTHER INFORMATION: Primer

<400> SEQUENCE: 50
gggaattctt ggaacaccaa tgggcat                                27

<210> SEQ ID NO 51
<211> LENGTH: 33
<212> TYPE: DNA
<213> ORGANISM: Artificial Sequence
<220> FEATURE:
<223> OTHER INFORMATION: Primer

<400> SEQUENCE: 51
ggccgtcgag tttttttgatt tcacgggttg ggg                        33

<210> SEQ ID NO 52
<211> LENGTH: 10
<212> TYPE: PRT
<213> ORGANISM: Artificial Sequence
<220> FEATURE:
<223> OTHER INFORMATION: Amino Acids 410-419 of uidA gene

<400> SEQUENCE: 52

Glu Gln Lys Leu Ile Ser Glu Glu Asp Leu
 1               5                  10

<210> SEQ ID NO 53
<211> LENGTH: 26
<212> TYPE: DNA
<213> ORGANISM: Artificial Sequence
<220> FEATURE:
<223> OTHER INFORMATION: Primer

<400> SEQUENCE: 53
ccgagctcga atgagtccat acttat                                 26

<210> SEQ ID NO 54
<211> LENGTH: 29
<212> TYPE: DNA
<213> ORGANISM: Artificial Sequence
<220> FEATURE:
<223> OTHER INFORMATION: Primer

<400> SEQUENCE: 54
ccgagctcaa aaccaatatg aatattata                              29

<210> SEQ ID NO 55
<211> LENGTH: 29
<212> TYPE: DNA
<213> ORGANISM: Artificial Sequence
<220> FEATURE:
<223> OTHER INFORMATION: Primer

<400> SEQUENCE: 55
ccgagctcta taaagacaat aaaaaaaat                              29

<210> SEQ ID NO 56
<211> LENGTH: 27
<212> TYPE: DNA
<213> ORGANISM: Artificial Sequence
<220> FEATURE:
<223> OTHER INFORMATION: Primer
```

```
<400> SEQUENCE: 56
ccctcgagaa acgtaacaat tttttt                                    27

<210> SEQ ID NO 57
<211> LENGTH: 25
<212> TYPE: DNA
<213> ORGANISM: Artificial Sequence
<220> FEATURE:
<223> OTHER INFORMATION: Primer

<400> SEQUENCE: 57
ccctcgagtt tcactttgag gtgga                                     25

<210> SEQ ID NO 58
<211> LENGTH: 28
<212> TYPE: DNA
<213> ORGANISM: Artificial Sequence
<220> FEATURE:
<223> OTHER INFORMATION: Primer

<400> SEQUENCE: 58
ccctcgagag aactaaatac tatatttc                                  28

<210> SEQ ID NO 59
<211> LENGTH: 27
<212> TYPE: DNA
<213> ORGANISM: Artificial Sequence
<220> FEATURE:
<223> OTHER INFORMATION: Primer

<400> SEQUENCE: 59
ccctcgagat atgacccaat atatctg                                   27

<210> SEQ ID NO 60
<211> LENGTH: 30
<212> TYPE: DNA
<213> ORGANISM: Artificial Sequence
<220> FEATURE:
<223> OTHER INFORMATION: Primer

<400> SEQUENCE: 60
acttgcttta gtttctgttt gtggtgacat                                30

<210> SEQ ID NO 61
<211> LENGTH: 27
<212> TYPE: DNA
<213> ORGANISM: Artificial Sequence
<220> FEATURE:
<223> OTHER INFORMATION: Primer

<400> SEQUENCE: 61
agaagtagta ggattggttc tcataat                                   27

<210> SEQ ID NO 62
<211> LENGTH: 21
<212> TYPE: DNA
<213> ORGANISM: Artificial Sequence
<220> FEATURE:
<223> OTHER INFORMATION: Primer

<400> SEQUENCE: 62
ccgccagcgt tcatcctgag c                                         21

<210> SEQ ID NO 63
```

```
<211> LENGTH: 11
<212> TYPE: DNA
<213> ORGANISM: Artificial Sequence
<220> FEATURE:
<223> OTHER INFORMATION: Consensus Sequence
<220> FEATURE:
<221> NAME/KEY: variation
<222> LOCATION: (0)...(0)
<223> OTHER INFORMATION: n at position 9 is a or g

<400> SEQUENCE: 63
catagaatna a                                                       11

<210> SEQ ID NO 64
<211> LENGTH: 10
<212> TYPE: DNA
<213> ORGANISM: Artificial Sequence
<220> FEATURE:
<223> OTHER INFORMATION: Consensus Sequence
<220> FEATURE:
<221> NAME/KEY: variation
<222> LOCATION: (0)...(0)
<223> OTHER INFORMATION: n at position 8 is a or g

<400> SEQUENCE: 64 atagaatnaa                                                         10
```

PLASTID PROMOTERS FOR TRANSGENE EXPRESSION IN THE PLASTIDS OF HIGHER PLANTS

CROSS-REFERENCES TO RELATED APPLICATIONS

The present application claims priority to International Application No. PCT/US98/11437, filed on Jun. 3, 1998 and published as International Publication No. WO98/55595, which claims priority to U.S. Provisional Application No. 60/048,376, filed on Jun. 3, 1997, and to U.S. Provisional Application No. 60/058,670, filed on Sep. 12, 1997, each of which is incorporated herein by reference in its entirety.

Pursuant to 35 U.S.C. §202(c) it is acknowledged that the U.S. Government has certain rights in the invention described herein, which was made in part with funds from the National Science Foundation, Grant Number MCB96-30763.

FIELD OF THE INVENTION

The present invention relates to plant genetic engineering and particularly to plastid transformation in higher plants. The invention provides novel promoter sequences useful for the expression of foreign genes of interest in various plant species.

BACKGROUND OF THE INVENTION

Chloroplast genes are transcribed by an RNA polymerase containing plastid-encoded subunits homologous to the α, β and β ' subunits of $E.\ coli$ RNA polymerase. The promoters utilized by this enzyme are similar to $E.\ coli$ $\sigma^{70}$-promoters consisting of −35 and −10 consensus elements (G. L. Igloi and H. Kossel, Crit. Rev. Plant Sci. 10, 525, 1992; W. Gruissem and J. C. Tonkyn, Crit. Rev. Plant. Sci. 12:-19, 1993) Promoter selection by the plastid-encoded RNA polymerase is dependent on nuclear-encoded sigma-like factors (Link et al. 1994, *Plant promoters and transcription factors*, Springer Verlag, Heidelberg, pp 63–83). In addition, transcription activity from some promoters is modulated by nuclear-encoded transcription factors interacting with elements upstream of the core promoter (L. A. Allison and P. Maliga, *EMBO J*., 14:3721–3730; R. Iratni, L. Baeza, A. Andreeva, R. Mache, S. Lerbs-Mache, *Genes Dev.* 8, 2928, 1994, Sun et al., *Mol. Cell Biol*. 9:5650–5659, 1989). These factors mediate nuclear control of plastid gene expression in response to developmental and environmental stimuli.

The existence of a second nuclear encoded polymerase transcription system in plastids has been demonstrated. However, the relevant nucleic acid sequences required for transcription initiation comprising the novel regulatory elements of this system have yet to be elucidated. It is an object of the present invention to provide these novel genetic elements. Incorporation of these regulatory elements into specific plastid directed DNA constructs enables greater flexibility and range in plant species available for plastid transformation, and facilitates ubiquitous expression of foreign proteins and/or RNAs and are useful in non-green plastids.

SUMMARY OF THE INVENTION

Promoters contain distinct DNA sequence information to facilitate recognition by the RNA polymerase and initiation of transcription leading to gene expression. In accordance with the present invention, promoters have been discovered which function in both monocots and dicots. These promoter elements may be used to advantage to express foreign genes of interest in a wider range of plant species. Additionally, the promoter elements of the invention drive expression of exogenous genes in non-green tissues. It is an object of the present invention to provide DNA constructs and methods for stably transforming plastids of multicellular plants containing such promoters. The DNA constructs of the invention extend the range of plant species that may be transformed.

The promoters recognized by plastid-encoded plastid RNA (PEP) polymerase have been well characterized in photosynthetic tissues such as leaf. The utility of PEP promoters for expression of foreign proteins in non-green tissues is demonstrated herein. The nuclear-encoded plastid (NEP) polymerase transcription system of the present invention directs expression of plastid genes also in roots, seeds, meristematic tissue and/or leaves. In most plants, including maize, cotton and wheat, plant regeneration is accomplished through somatic embryogenesis (i.e., involving meristematic tissue). In a preferred embodiment of the invention, efficient plastid transformation in these crops will be greatly facilitated, through the use of the NEP and PEP plastid transcription system and promoters of the present invention.

Particularly preferred promoters for use in the constructs of the invention are the clpP -111 (SEQ ID NOS: 15, 16, 30 and 31) promoters for the transformation of monocots and dicots and the pclp -53 promoter for transformation in dicots. Homologous clpP promoters from other plant species are contemplated to be within the scope of the present invention.

Other preferred promoters for use in expressing foreign genes of interest in the plant plastid in non-green tissues are PEP promoters present in the 16SrDNA operon, SEQ ID NOS: 28 and 29. Additional promoter elements suitable for use in the present invention are the rpoB and atpB promoters.

The NEP promoters of the invention are incorporated into currently available plastid transformation vectors such as those described in pending U.S. application Ser. No. 08/189, 256, and also described by Svab & Maliga., *Proc. Natl. Acad. Sci. USA*, 90, 913 (1993). Protocols for using such vectors are described in U.S. Pat. No. 5,451,513. The disclosures of the three references cited above are all incorporated by reference herein. To obtain transgenic plants, plastids of non-photosynthetic tissues are transformed with selectable marker genes expressed from NEP promoters and transcribed by the nuclear-encoded polymerase. Likewise, to express foreign proteins of interest, expression cassettes are constructed for high level expression in non-photosynthetic tissue, using the NEP promoter transcribed by the nuclear-encoded plastid RNA polymerase. In another aspect of the invention, PEP promoters of the invention are incorporated into currently available plastid transformation vectors and protocols for use thereof.

In yet another aspect of the invention, the NEP transcription system also may be combined with the $\sigma^{70}$-type system through the use of dual NEP/PEP promoters. In transforming DNA constructs, the promoters are arrayed in tandem, operably linked to the coding region of the foreign gene of interest. As used herein, the term transcription unit refers to isolated DNA segments which comprise the essential coding regions of one or more exogenous protein(s) of interest. Such transcription units may also contain other cis elements for enhancing gene expression, such as enhancer elements. Transcription units are operably linked to the promoters of the invention, such that expression of the transcription unit is regulated by said promoter. Particularly preferred promoters for use in combination are the Prrn PEP promoters combined with the clpP type II NEP promoter in dicots and the Prrn PEP promoter combined with the clpP Type I NEP promoter for use in both monocots and dicots. A suitable Prrn promoter has the following sequence (SEQ ID NO: 32) 5'-GCTCCCCCGC CGTCGTTCAA TGAGAATGGA TAAGAGGCTC GTGGGATTGA CGTGAGGGGG CAGGGATGGC TATATTCTG GGAGCGAACT CCGGGCGAAT ACGAAGCGCt TGGATACAGT TGTAGGGAGG GATT-3'.

Homologous PEP and NEP promoters from a variety of plant species corresponding to those listed above are also considered to fall within the scope of the present invention. The transforming DNA also contains 3' regulatory regions of plant or bacterial origin to effect efficient termination of transcription. An exemplary 3' regulatory region is shown in FIG. 13, SEQ ID NO: 27.

BRIEF DESCRIPTION OF THE DRAWINGS

FIG. 2B is an autoradiograph showing the results of an in vitro capping and RNase protection assay to identify primary transcript 5' ends. Note that the RNase protection construct is short and protects only a 79 nt fragment. Size of molecular weight (MW) markers (100, 200, 300, 400, and 500 nucleotides) is also shown.

FIG. 3A is an autoradiograph showing the results of primer extension analysis of RNA from green (G) and white (W) iojap maize leaves. The number –147 refers to transcript 5'-end. FIG. 3B shows the results of an in vitro capping and RNase protection assay to identify primary transcript 5'-ends. Note that the RNase protection construct is short and protects only a 74 nt fragment. Size of molecular weight (MW) markers (100, 200, 300, 400, and 500 nucleotides) is also shown.

FIGS. 4A, 4B and 4C show the mapping of atpB promoters. FIG. 4A show the results of primer extension analysis of RNA from green (G) and white (W) iojap maize leaves. Number –298 and –601 refer to transcript 5'-ends. FIG. 4B shows the results of an in vitro capping and RNase protection assay to identify primary transcript 5' ends. Note that the RNase protection construct is short and protects only a 79 nt fragment. Size of molecular weight (MW) markers (100, 200, 300, 400, and 500 nucleotides) is also shown. FIG. 4C depicts a physical map of the atpB—rbcL intergenic region. Map position of the primary transcript 5' ends for NEP and PEP promoters are marked with filled and open circles, respectively.

FIGS. 5A–5D. FIG. 5A shows the alignment of DNA sequences flanking the NEP promoter transcription initiation sites. Site of transcription initiation is marked (filled circles). Regions with significant similarity are boxed (Box I and Box II). Sequences corresponding to the loose 10-nt dicot NEP consensus are underlined with thin lines. clpP -111 promoter region is maize is indicated by the thick underlining. FIG. 5A shows rpoB (SEQ ID NO: 1), atpB (SEQ ID NO: 2) and clpP (SEQ ID NO: 3) promoter regions, respectively in maize. The alignment and nucleotide sequences of atpB promoters in maize, sorghum, barley, wheat, and rice are shown in FIG. 5B and correspond to SEQ ID NOS: 4, 5, 6, 7 and 8 respectively. FIG. 5C shows the alignment of the rpoB sequences in maize (SEQ ID NO: 9), rice (SEQ ID NO: 10) and tobacco (SEQ ID NO:11). The alignment of the clpP sequences in maize (SEQ ID NO: 12), rice (SEQ ID NO: 13), and wheat (SEQ ID NO: 14 is shown in FIG. 5D.

FIG. 6 shows the sequence alignment of the tobacco (SEQ ID NO: 15) and rice (SEQ ID NO: 16) plastid clpP promoter regions. The NEP transcription initiation sites are marked with filled circles, the PEP transcription initiation site is marked with an open circle. The third tobacco NEP promoter is outside the sequence shown. The clpP coding regions are boxed. The 29-bp shared homologous region around the Type II tobacco PclpP-53 promoter is underlined.

FIG. 8A shows the results of primer extension analysis to map RNA 5'-ends upstream of the rice PclpP::uidA::Trps16 chimeric gene. Primer extension analysis was carried out on total cellular RNAs isolated from the leaves of wild-type (wt) and transplastomic (T) tobacco plants. The numbers (−61, −111, −136, −169, 177) refer to nucleotide positions of the mapped 5' ends relative to the ATG translation initiation codon of the rice clpP gene. FIG. 8B shows a schematic representation of RNA 5' ends mapped in the rice clpP promoter region in rice (Os) and in tobacco (Os in Nt), and upstream of the wild-type tobacco clpP gene (Nt). Promoters identified in homologous systems are marked (NEP, filled circles, PEP, open circles). Numbers indicate distance from translation initiation codon (nucleotide upstream of ATG is position −1).

FIG. 9 depicts an alignment of DNA sequences which are conserved around the plastid clpP transcription initiation sites. Sequences are aligned for Marchantia polymorpha (Kochi) (SEQ ID NO: 18), Pinus contorta (Clarke) (SEQ ID NO: 19), spinach (Westhof) (SEQ ID NO: 20), tobacco (Hajdukiewicz et al., 1977) (SEQ ID NO: 21), rice (SEQ ID NO: 22), maize (SEQ ID NO: 23) and Arabidopsis (SEQ ID NO: 24). Wild-type RNA 5' ends are marked with filled circles. The −61 5' end of the rice clpP-uidA chimeric mRNA is marked with an asterisk. Conserved nucleotides are boxed if identical at least in five species. The translation start codons are shaded.

FIGS. 13A–B show the DNA sequence (SEQ ID NO: 27) of the chimeric uidA gene. SacI and HindIII cloning sites are marked. SacI, XhoI, NcoI, XbaI and HindIII sites are underlined. Translation initiation (ATG) and stop (TGA) codons are underlined twice. Nucleotides derived from the tobacco plastid genome are in capital letters; the position of the first and last nucleotide within the genome is listed.

FIG. 17A–17B. FIG. 17 shows the alignment of the maize (SEQ ID NO: 28 and rice (SEQ ID NO: 29) PEP promoter in the rrn operon, FIG. 17A. FIG. 17B shows the alignment of the plastid clpP promoter regions in maize (SEQ ID NO: 30) with the homologous regions in rice (SEQ ID NO: 31). PEP (○) and NEP (●) transcription initiation sites and processed 5' ends (−) are marked. For 16SrDNA sequence information see Strittmatter et al. (1985). The present invention provides sequence information for maize clpP.

DETAILED DESCRIPTION OF THE INVENTION

Figure 1:
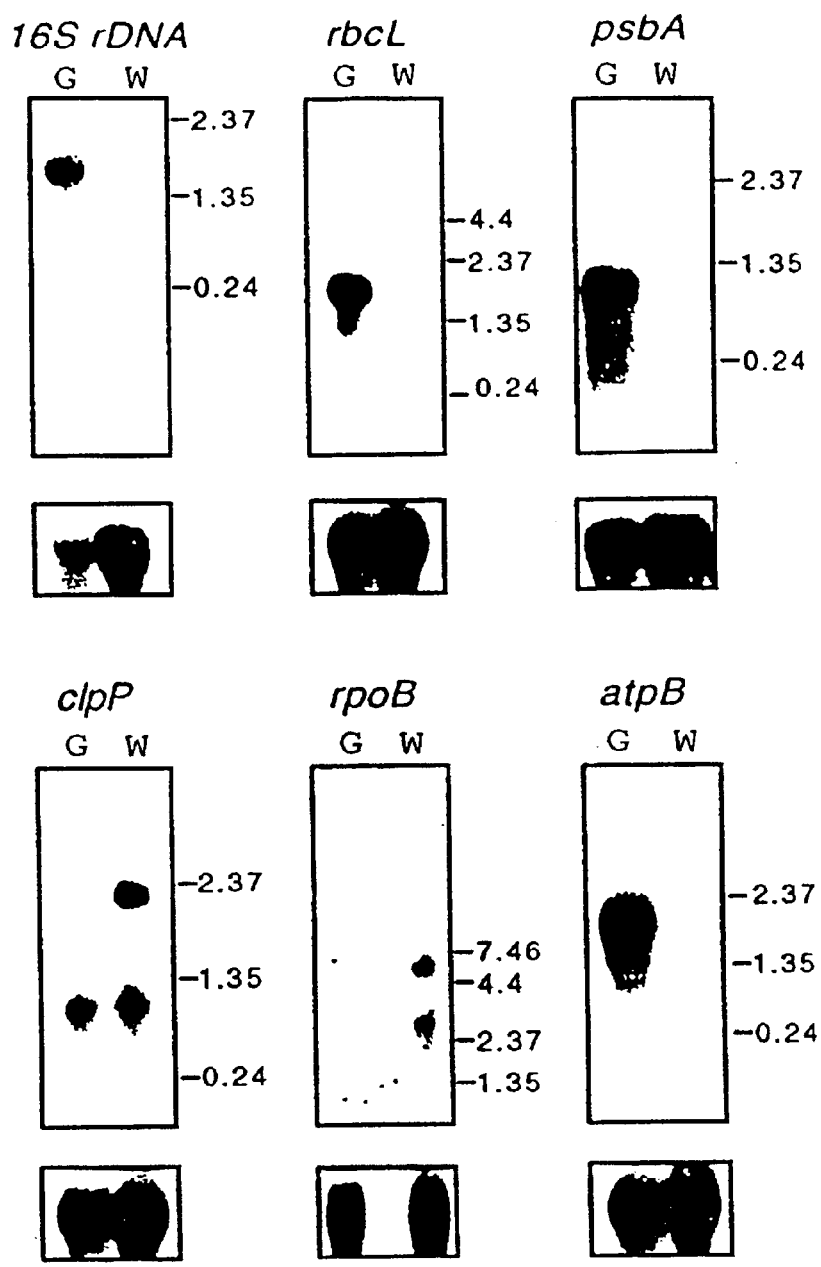
FIG. 1 depicts a series of autoradiographs illustrating RNA steady state concentrations in green (G) and white (W) iojap maize leaves. To control for loading, blots shown above were reprobed for cytoplasmic 25S ribosomal RNA as described (Dempsey et al., *Mol. Plant Path*. 83:1021–1029, 1993) (lower panels).

Several reports have suggested the existence of an additional plastid-localized, nuclear-encoded RNA polymerase (reviewed in Gruissem and Tonkyn, 1993; Igloi and Kossel, 1992; Mullet, 1993; Link, 1994). By deleting the rpoB gene encoding the essential β subunit of the tobacco E. coli-like RNA polymerase, the existence of a second plastid transcription system which is encoded by the nucleus has been established (Allison et al., 1996, EMBO J. 15:2802–2809). Deletion of rpoB yielded photosynthetically defective, pigment-deficient plants.

While the activity of the previously-known plastid-encoded $\sigma^{70}$-type transcription system in photosynthetically active tissues, such as leaf, has been the subject of much research, the nuclear-encoded polymerase transcription system has not yet been characterized. In accordance with the present invention, it has been discovered that the NEP system also directs expression in roots, seeds and meristematic tissue. In most plants, including maize, cotton and wheat, plant regeneration is accomplished through somatic embryogenesis (i.e., involving meristematic tissue). Efficient plastid transformation in these crops will be enabled, or greatly facilitated, through the use of clpP promoters driven by the NEP plastid transcription system of the present invention.

The ATP dependent Clp protease is widespread, if not ubiquitous, among both procaryotic and eucaryotic cells (Goldberg, Eur. J. Biochem. 203:9–23, 1992). Clp protease expression has recently been examined in chlamydomonas (Huang et al. Mol. Gen. Genetics 244:151–159, 1994). The results of gene knockout experiments in this unicellular algae demonstrated the following: 1) all the transformants were found to be heteroplasmic mutants containing both the disrupted clpP and wild-type copies; 2) the transformants persisted as heteroplasmic mutants after six rounds of growth and screening under selection pressure for the disrupted clpP; and 3) the heteroplasmic mutant stabilized at a level where approximately 80% of the clpP DNA copies were disrupted. These data indicate that the clpP is essential for cell growth even under conditions where photosynthesis is not required.

Shanklin et al. have examined the immunolocalization of clpP protein in Arabidopsis chloroplasts (Shanklin et al. The Plant Cell 7:1713–1722, 1995). These studies revealed that clpP and clpC are constitutively expressed in all tissues of Arabidopsis at levels equivalent to those of E. coli clpP and clpA. The observation that the clpP NEP promoter drives constitutive gene expression in all parts of a plant makes this promoter particularly suitable for use in the present invention.

The NEP promoters of the invention are incorporated into currently available plastid transformation vectors such as those described in pending U.S. application Ser. No. 08/189, 256, and also described by Svab & Maliga., Proc. Natl. Acad. Sci. USA, 90, 913 (1993). Protocols for using such vectors are described in U.S. Pat. No. 5,451,513. The disclosures of the three references cited above are all incorporated by reference herein. To obtain transgenic plants, plastids of non-photosynthetic tissues as well as photosynthetic tissues are transformed with selectable marker genes expressed from NEP promoters and transcribed by the nuclear-encoded polymerase. Likewise, to produce foreign proteins of interest, expression cassettes are constructed for high level expression in non-photosynthetic tissue, using the clpP NEP promoter transcribed by the nuclear-encoded plastid RNA polymerase. The NEP transcription system also may be combined with the σ⁷⁰-type system through the use of dual NEP/PEP promoters.

For versatility and universal applications, expression of selectable marker genes for plastid transformation is desirable in all targeted tissue types at a high level. Selectable marker genes in the currently utilized plastid transformation vectors are expressed from PEP promoters recognized by the plastid encoded RNA polymerase. The PEP polymerase transcribes photosynthetic genes and some of the housekeeping genes, and therefore appears to be the dominant RNA polymerase in photosynthetically active leaf tissues. Efficient plastid transformation has been achieved in tobacco based on chloroplast transformation in leaf cells. However, plant regeneration is not feasible, or is not practical from the leaves of most agronomically important cereal crops, including maize, rice, wheat and in cotton. In these crops, transgenic plants are typically obtained by transforming embryogenic tissue culture cells or seedling tissue. Given that these tissues are non-photosynthetic, expression of marker genes by constitutive clpP NEP promoters which are active in non-green tissues will facilitate transformation of plastids in all non-photosynthetic tissue types. Furthermore, as demonstrated herein, the ribosomal RNA operon PEP promoter is highly active in rice embryogenic cells.

The following nonlimiting Examples describe the invention in greater detail. Specifically, Examples I–III below describe preferred methods for making and using the DNA constructs of the present invention and for practicing the methods of the invention. Any molecular cloning and recombinant DNA techniques not specifically described are carried out by standard methods, as generally set forth, for example, in Ausubel (ed.), Current Protocols in Molecular Biology. John Wiley & Sons, Inc.(1994).

EXAMPLE I

Identification of Promoters for the Nuclear-encoded Plastid RNA Polymerase in the Ribosome-deficient Maize Mutant Iojap As described previously, plastid promoters with conserved -10/-35 elements are well characterized for the plastid-encoded plastid RNA polymerase, PEP. Additionally, a ten-nucleotide promoter consensus was reported for a second, nuclear encoded, plastid RNA polymerase, NEP, in tobacco, a dicot (Hajdukeiwicz et al. 1997, in press). In this Example, NEP promoters active in monocots are described. NEP promoter mapping was carried out in the plastid ribosome-less maize mutant iojap which lacks PEP. These studies have revealed that atpB, an ATPase subunit gene, contains promoters for both NEP and PEP. In contrast, clpP, a protease subunit gene, and the rpoB operon, encoding the rpoB, rpoC1 and rpoC2 PEP subunit genes, are transcribed from NEP promoters only. These findings suggest conservation of transcription systems between monocots and dicots for the expression of certain plastid genes. The monocot NEP promoters share sequence homology around the transcription initiation site, including the 10-nucleotide loose consensus identified in dicots.

In the plastids of photosynthetic higher plants, genes are transcribed by at least two RNA polymerases: the plastid-encoded plastid RNA polymerase (PEP) and the nuclear-encoded plastid RNA polymerase (NEP). The sigma-factor homologues and PEP regulatory factors are encoded in the nucleus and are imported into plastids (Igoli and Kossel, (1992) supra; Link, (1996) Bioessays 18:465–471; Stern D B, Higgs D C, Yang J (1997) Trends Plant Sci 2:308–315). Much less is known about NEP. One appealing candidate for NEP is a 110 kD protein which has biochemical properties similar to yeast mitochondrial and T7 RNA polymerases. NEP may require accessory factors, such as CDF2 for its activity (Lerbs-Mache, 1993; Iratni et al., 94; Genes and dev).

Dicot promoters for NEP were identified in tobacco plants lacking PEP due to deletion of rpoB encoding the PEP β subunit. The general rule emerging from these studies is that plastid genes fall into three classes. Class I genes contain only PEP promoters. Examples of this class are the photosytem I and II genes. Class II genes contain both NEP and PEP promoters. Representative members of this class of genes are genes involved in plant metabolism and housekeeping genes. Genes in the third class contain NEP promoters only. Genes in this class include rpoB and accD.

As plastid transformation is not yet available in monocots, ΔrpoB plants could not be obtained for maize NEP promoter analysis. However, mutants with a defect in plastid ribosome accumulation are available in barely (albostrians; Hess et al., EMBO J. 12:563–571, 1993) and maize (iojap; Walbot and Coe, Proc. Natl. Acad. Sci. 76:2760–2764, 1979; Han et al., Planta 191:552–563, 1993; Han et al., EMBO J. 11:4037–4046, 1992). In the absence of plastid ribosomes, these mutants cannot synthesize PEP. Both mutants accumulate mRNAs for a subset of plastid genes indicating the presence of NEP activity (Hess et al., 1993, supra; Han et al., 1993, supra).

NEP promoters for three plastid genes were mapped in white ribosome-less maize iojap seedlings. The data show that the maize atpB gene has alternative NEP and PEP promoters while the clpP and the rpoB genes are transcribed from NEP promoters exclusively in both white and green seedlings. DNA sequence alignment revealed that monocot NEP promoters share homology directly upstream of the transcription initiation site. The homologous region includes the previously identified tobacco NEP promoter consensus elements suggesting conservation of the NEP transcription machinery between monocots and dicots.

Materials and Methods for Example I

Plant Materials. Iojap is a recessive striped mutant of maize. Maternal white and green seedlings were obtained by crossing a striped ij/ij maternal parent (1404) with pollen from a wild type male (inbreed Oh51a). The seeds were kindly provided by Rob Martienssen and Mary Byrne, Cold Spring Harbor Laboratory. Surface-sterilized seeds were germinated in vitro on 2% MS medium (24° C., 16 hours illumination).

RNA Gel blots. Total cellular RNA was prepared from the leaves of 9-day-old seedlings (Stikema et al. Plant Mol. Biol. 11:255–269, 1988). The RNA (5 μg per lane) was electrophoresed on 1% agarose/formaldehyde gels, then transferred to Hybond N (Amersham) using the Posiblot Transfer apparatus (Stratagene). Hybridization to random-primer labeled fragment was carried out in Rapid Hybridization Buffer (Amersham) overnight at 65° C.

Double-stranded ptDNA probes were prepared by random-primed ³²P-labeling of PCR-generated or gel-purified DNA fragments. The sequence of the primers used for PCR, along with their positions within the tobacco (N.t.; Genebank Accession No. Z00044) or maize (Z.m.; Genebank Accession No. X86563) ptDNA are as follows:

| Gene | | 5' nt position in ptDNASequence | | SEQ ID NO: |
|---|---|---|---|---|
| atpB | (Z.m.) | 55860 (C) | GAGAGGAATGGAAGTGATTGACA | (33) |
| | | 55103 | GAGCAGGGTCGGTCAAATC | (34) |
| clpP | (Z.m.) | 69840 | ATCCTAGCGTGAGGGAATGCTA | (35) |
| | | 70064 (C) | AGGTCTGATGGTATATCTCAGTAT | (36) |
| psbA | (N.t.) | 1550 (C) | CGCTTCTGTAACTGG | (37) |
| | | 667 | TGACTGTCAACTACAG | (38) |

The following ptDNA fragments were used as probes: rbcL(N.t.), a BamHI fragment (nucleotides 58047 to 59285 in ptDNA); 16SrDNA (N.t.), EcoRI to EcoRV fragment (nucleotides 138447 to 140855 in the ptDNA); rpoB, HindIII fragment (nt 24291–24816).

Primer extension analysis. Primer extension reactions were carried out on 10 μg of total leaf RNA as described (Allison et al. *EMBO J.* 15:2802–2809, 1996). The primers are listed below, with nucleotide positions in the published maize plastid genome sequence (Maier et al., *J. Mol. Biol.* 251:614–628, 1995). Underlined oligonucleotides (added to create cloning site) were also used to generate the capping constructs, in which case the position of the first nucleotide in the genome sequence is positioned immediately following the underline.

rpoB) or EcoRI (clpP) site (underlined) downstream of the amplified sequence. The amplified product was cloned after digestion with the appropriate restriction enzyme into a pBSKS+ vector (Stratagene). To generate unlabeled RNA complementary to the 5' end of RNAs, the resulting plasmid was linearized with XhoI (atpB, rpoB) or EcoRI (clpP) and transcribed in a Megascript (Ambion) reaction with T7 RNA polymerase. Markers (100, 200, 300, 400, and 500 nucleotides) were prepared with the RNA Century Markers Template Set (Ambion), following the manufacturer's protocol.

DNA sequence analysis. DNA sequence analysis was carried out utilizing the Wisconsin Sequence Analysis Package (Genetics Computer Group, Inc.).

| Gene | 5' nt position in ptDNA | Sequence | SEQ ID NO: |
|---|---|---|---|
| clpP#1 | 70182 | GGTACTTTTGGAACACCAATGGGCAT | (39) |
| atpB#1 | 56095 | GAAGTAGTAGGATTGGTTCTCATAAT | (40) |
| atpB#2 | 56640 | GGTCTAGAATTCCTATCGAATTCCTTC | (41) |
| rpoB#1 | 21545 (C) | GAATCTACAAAATCCCTCGAATTG | (42) |
| rpoB#2 | 21418 (C) | ACTCTTCATCAATCCCTACG | (43) |

(Note: C at 3'-end of the atpB#2 oligonucleotide is at nt position 56644; the published sequence has a 15 nucleotide deletion relative to the sequence we found).

Identification of primary transcripts by in vitro capping. Total leaf RNA (20 μg for clpP or 100 μg for rpoB and atpB transcripts) from white seedlings was capped in the presence of 0.25 or 1.0 mCi [α-$^{32}$P] GTP (Kennell and Pring, *Mol. Gen. Genet.* 216:16–24, 1989). Labeled RNAs were detected by ribonuclease protection (Vera et al., *Plant Mol. Biol.* 19:309–311, 1992) using the RPAII kit (Ambion). To prepare the protecting complementary RNA, an appropriate segment of the plastid genome was PCR-amplified using the primers listed below.

Results and Discussion

Plastid Transcript Accumulation in the Maternal White and Green Maize Plants.

Lack of 16S rRNA accumulation in the white maize plants confirmed the reported lack of plastid ribosomes in the white iojap seedlings (Walbot and Coe 1979, supra). The absence of rbcL and psbA mRNAs, known to be transcribed from PEP promoters, indicates that the maternal white plants indeed lack PEP activity. (Han et al., 1993, supra). See FIG. 1.

| Gene | 5' nt position in ptDNA | Sequence | SEQ ID NO: |
|---|---|---|---|
| clpP#2 | 70241 | GGTCTAGACTACACTTTAATATGGA | (44) |
| clpP#3 | 70549 (C) | GGGAATTCTGTTTGTAAGAAGA | (45) |
| atpB#2 | 56640 | GGTCTAGAATTCCTATCGAATTCCTTC | (46) |
| atpB#3 | 56832 (C) | GGCTCGAGGGACAACTCGATAGGATTAGG | (47) |
| rpoB#3 | 21394 (C) | GGTCTAGAATCTAGCAATCATGGAATC | (48) |
| rpoB#4 | 21066 | GGCTCGAGCGTGCTATTCTAAATCGT | (49) |

The 5' primers set forth above were designed to add a XbaI restriction site (underlined) upstream of the amplified fragment. The 3' primers were designed to add a XhoI (atpB, Transcript accumulation for three additional plastid genes: clpP, rpoB and atpB has been analyzed in iojap plants. High steady-state mRNA levels, indicating the presence of NEP promoters was reported for these genes in iojap maize (Han et al., 1993, supra), albostrians barley (Hess et al., 1993, supra) and ΔrpoB tobacco (Hajdukiewicz et al., EMBO J., in press, 1997), respectively. Readily-detectable accumulation of mRNA in the ribosome-less iojap plants confirmed that active NEP promoters regulate expression for each of these genes (FIG. 1).

The clpP NEP Promoter is Efficiently Transcribed in White and Green Seedlings.

To identify the NEP promoters, transcript 5'-ends were mapped by primer extension analysis. To distinguish between 5'-ends that represent transcripts from NEP promoters from those generated by RNA processing, the 5'-ends were capped using guanylyltransferase.

Figure 2A:
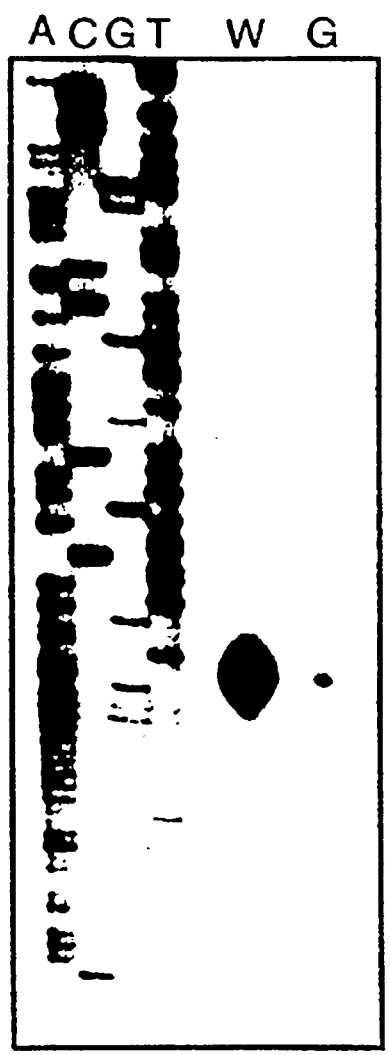
FIGS. 2A and 2B depict a pair of autoradiographs showing the results of primer extension analysis on green (G) and white (W) iojap maize leaves for the mapping of the clpP promoter, FIG. 2A. The number –111 refers to the transcript 5' end relative to the ATG translation initiation codon.
Figure 2B:
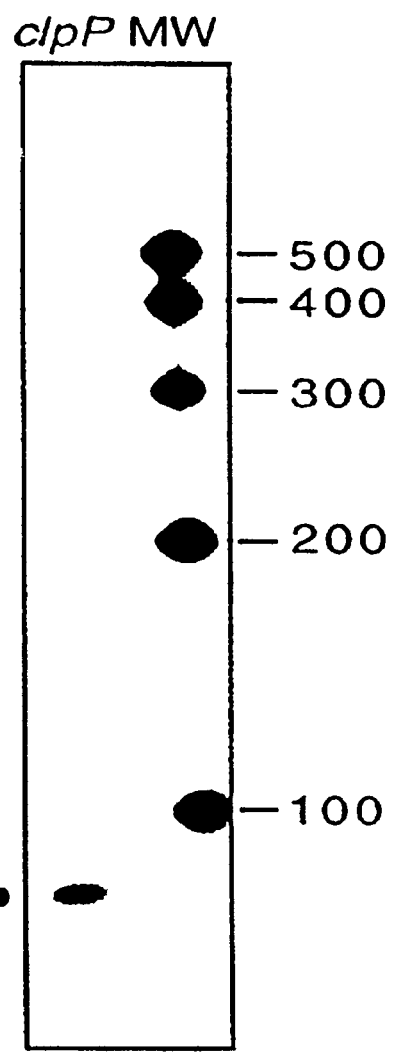

For clpP, significant mRNA accumulation was found in both white and green seedlings. Primer extension analysis identified only one major clpP 5'-end at nucleotide position –111 (the nucleotide upstream of the ATG being at –1 position). The clpP-111 transcript could be capped in vitro. See FIG. 2B. These data confirm that this 5' end is a primary transcript and also identifies the maize NEP promoter PclpP-111. The same 5'-end is observed in both white and green maize seedlings indicating that the same clpP promoter is active in chloroplasts as well as in the nonphotosynthetic iojap plastids (FIG. 2A). Therefore, PclpP-111 is considered to be a constitutive promoter. In rice, the clpP transcript 5'-end mapped to the same nucleotide indicating conservation of PclpP-111 in monocots (data not shown).

The rpoB NEP Promoter Activity is Enhanced in Iojap Plastids.

Figure 3A:
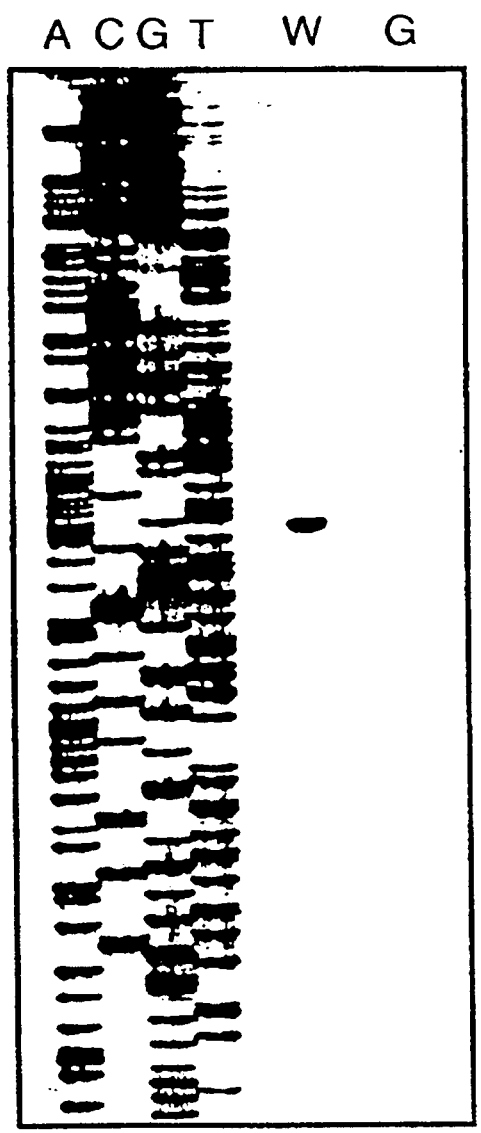
FIGS. 3A and 3B show the mapping of maize rpoB promoters.
Figure 3B:
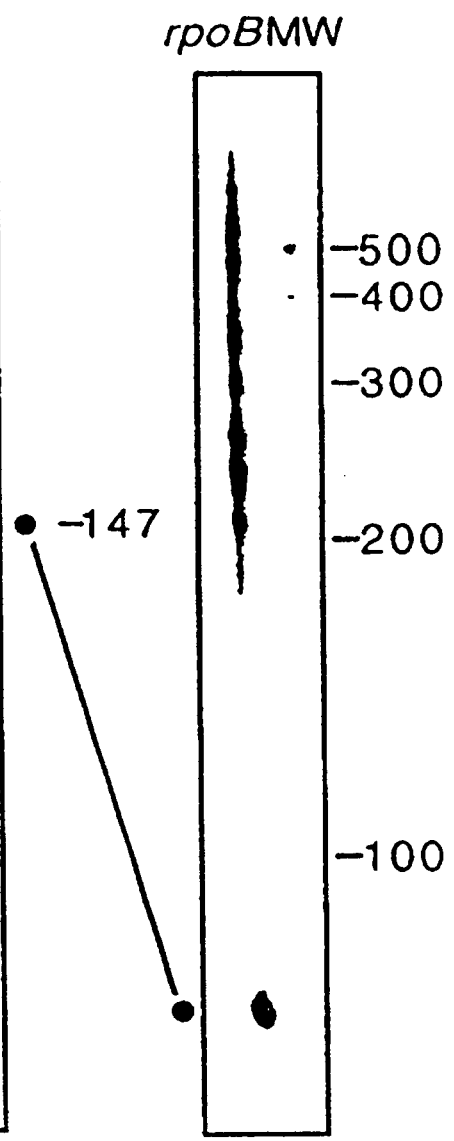

RNA gel blot analysis shows that rpoB mRNA accumulates to a detectable level only in white seedlings (FIG. 1). However, more sensitive primer extension analysis revealed that the same 5'-ends were present in both white and green leaves. Two 5'-ends could be identified, a major band at nucleotide position –147, and a minor band at position –285 (FIG. 3A). The in vitro capping assay confirmed that the –147 RNA species is a primary transcript (FIG. 3B), and therefore the product of PrpoB-147 promoter.

The atpB Gene is Transcribed from a NEP Promoter in White Plants and from a PEP Promoter in Green Seedlings.

There is substantial atpB mRNA accumulation in green leaves, while much less is found in the white iojap leaves (FIG. 1). Primer extension analysis of mRNA from green leaves identified a transcript with a 5'-end at nucleotide position –298 (FIG. 4A) confirming an earlier report (Mullet et al., Plant Mol. Biol. 4:39–54, 1985). This –298 mRNA species was absent in leaf RNA isolated from white plants, indicating that the –298 mRNA is a PEP transcript. Instead, another atpB transcript was mapped to nucleotide position –601 (FIG. 4A). The difference in the size of the two mRNAs is apparent on the RNA gel blot shown in FIG. 1.

The –601 transcript could be capped in vitro by guanylyltransferase, indicating that it is a primary transcript (FIG. 4B). Therefore, it is the product of the PatpB-601 NEP promoter, with readily detectable activity only in white iojap leaves.

Sequence Conservation Around the Monocot NEP Transcription Initiation Sites.

Alignment of the maize clpP, rpoB and atpB NEP promoters revealed significant homology upstream of the transcription initiation sites. In a 13-nucleotide region 8 nucleotides are shared in all three promoters (FIG. 5; Box I). In a pairwise comparison, atpB/clpP, atpB/rpoB and clpP/rpoB share 11, 10 and 8 nucleotides, respectively. In addition, atpB and clpP share 8 out of 9 nucleotides further upstream (–21 to –30 relative to transcription initiation site; Box II in FIG. 5).

Interestingly, each maize NEP promoter has sequence similarity around the transcription initiation site with the loose dicot NEP promoter consensus CATAGAATA/GAA (SEQ ID NO:63) (Hajdukiewicz et al., 1997, supra; underlined in FIG. 5). For clpP, 9 nucleotides are conserved out of 10; for atpB and rpoB, the number of conserved nucleotides is 7 out of 10 (FIG. 5). In addition, a second conserved region (Box II, FIG. 5) is found upstream of Box I in atpB and clpP, but not in the rpoB promoters. Interestingly, the monocot Box II contains truncated versions of the dicot NEP consensus in a direct orientation: 7 out of 10 bp match in case of the maize clpP (ATAGAAT) and atpB (AT-GAATA) genes (FIG. 5). These tandem repeats may play a role in regulating NEP promoter activity.

The regions containing the tentative maize NEP promoter sequences (–30 to +25) have been aligned with homologous regions from other monocot plants. See FIG. 5B–5D. The high degree of sequence conservation indicates the presence of functional promoters in each of these monocots species. Promoter activity for the rice homologue of the maize PclpP-111 promoter has been confirmed by primer extension analysis (data not shown).

The data reported herein show that maize plastid NEP promoter regions share sequence homology around the transcription initiation site with the conserved CATAGAATA/GAA (SEQ ID NO:63) NEP sequence motif in tobacco (FIG. 5). Therefore, these promoters are considered to be Type I NEP promoters. This finding indicates conservation of the NEP transcription machinery between monocots and dicots. Sequences upstream of the transcription initiation sites are conserved more extensively than downstream sequences among the maize clpP, rpoB, and atpB promoters, as shown in FIG. 5, similar to the dicot Type I NEP promoters (Hajdukiewicz et al., 1997, supra).

Both, the maize PclpP-111 promoter and the tobacco PclpP-53 promoter are constitutive. In contrast to the maize promoter, the clpP promoter region in tobacco lacks the CATAGAATA/GAA (SEQ ID NO:63) sequence motif (Hajdukiewicz et al., 1997, supra) suggesting recognition by a different NEP specificity factor (Type II NEP promoter). Interestingly, in Type II NEP promoters sequences downstream of the transcription initiation sites are conserved more extensively than upstream as described in the following example. The tobacco PclpP-53 promoter homologues are the only known examples for plastid Type II NEP promoters. They have been highly conserved during evolution, including the liverworth Machantia polymorpha and the conifer Pinus contorta. Although DNA sequences required for clpP Type II NEP promoter function are maintained, this region is transcriptionally silent in maize, rice and wheat. Lack of transcription from this region in cereals is probably due to the loss of Type II recognition specificity. See Example II. Accordingly, the tobacco (dicot) Type II clpP promoter is suitable to drive the expression of plastid transgenes only in dicots, whereas the cereal Type I promoter may be useful in both monocots and dicots.

The rpoB operon is one of few genes known to be expressed by NEP only. The PrpoB-147 is a Type I NEP promoter but, unlike clpP and atpB, lacks Box II (FIG. 5). Accumulation of mRNA from this promoter is low in mature leaves due to down-regulation of transcription rates (Baumgartner et al., Plant Physiology 101:781–791, 1993). The PrpoB –147 promoter identified in this study probably plays a central role in plastid development since it regulates expression of four out of the five plastid-encoded PEP subunits (Shimada et al., Mol. Gen. Genet. 221:395–402, 1990). According to one model, the two RNA polymerases form a developmental cascade during chloroplast differentiation. During the early stages of plastid development, plastid genes encoding the plastid's transcription and translation apparatus would be transcribed NEP. Once PEP is made, it would initiate transcription of photosynthetic genes from PEP promoters, and take over transcription of housekeeping genes from alternative PEP promoters (Hess et al., 1993, supra; Lerbs-Mache, Proc. Natl. Acad. Sci. 90:5509–5513, 1993; Mullet, Plant Physiol. 103:309–313, 1993; Hajdukiewicz et al. 1997, supra). Consistent with this model is transcription of rpoB from a NEP promoter. However, in maize at least one gene, clpP, is exclusively and efficiently transcribed by NEP in mature chloroplasts indicating that NEP remains active and essential for cellular functions even if PEP is present. An alternative hypothesis is proposed herein, which assumes that NEP and PEP are constitutively present all the time and selective transcription is mediated by promoter-specific transcription factors. The identification of NEP promoters for dicots (Hajdukiewicz et al., 1997, supra) and monocots (described herein) facilitates the elucidation of the roles these two plastid RNA polymerases play in plastid function and development.

EXAMPLE II

Altered clpP Promoter Recognition by the Nucleus-Encoded Plastid RNA Polymerase Suggests Loss of a Conserved Plastid Transcription Factor in Monocots The plastid clpP gene is transcribed by the nuclear-encoded plastid RNA polymerase (NEP) in rice, a monocot, and tobacco, a dicot. However, the two NEP promoters do not share sequence homology. To assess conservation of NEP promoter recognition between monocots and dicots, a reporter gene (uidA) expressed from the rice clpP promoter region has been introduced into tobacco plastids. The data indicate that in tobacco, transcription initiates at the correct site from the rice clpP promoter. Thus, NEP promoter recognition for this gene is conserved in both monocots and dicots. Surprisingly, transcription from the rice sequence initiated at a second site, which possesses a short stretch of homologous sequence similar to the tobacco clpP promoter region. Sequences around the clpP transcription initiation site are conserved in tobacco, a dicot, Marchantia polymorpha, a bryophyte, and Pinus contorta, a conifer. Lack of transcription from this region in rice and other cereals indicates the evolutionary loss of a factor required for NEP Class II promoter specificity.

Materials and Methods for Example II
Construction of Plasmid pDS44.

Plasmid pDS44 is a pLAA24 derivative (Zoubenko et al., Nucleic Acids Res. 22:3819–3824, 1994) which carries a uidA reporter gene expressed from a Prrn promoter. Plasmid pDS44 was obtained by excising the Prrn promoter as an SacI/EcoRI fragment and replacing it with the rice clpP promoter region engineered as a SacI/EcoRI fragment. The 251 nucleotide SacI/EcoRI DNA fragment containing the rice clpP promoter region (including 19 basepairs of the coding region) was obtained by PCR amplification. The sequence of the PCR primers, and the position of their first nucleotide (or of its complement) in the rice plastid genome (Hiratsuka et al., Mol. Gen. Genet. 217:185–194, 1989; GeneBank Accession No. X15901) are:

| P1 | 68520 (C) | gggagcTCGAATCACCATTCTTT | SEQ ID NO: 50 |
| P2 | 68270 | gggaattcTTGGAACACCAATGGGCAT | SEQ ID NO: 51 |

Nucleotides derived from the plastid genome are in capital letters; those included to create a restriction site are in lower case letters. SacI or EcoRI restriction sites are underlined.

Tobacco plastid transformation. Plastid transformation and regeneration of transgenic tobacco plants was carried out according to the protocol described by Svab and Maliga (Proc. Natl. Acad. Sci. 90:913–917, 1993). Briefly, tobacco leaves were bombarded with tungsten particles coated with plasmid pDS44 DNA using the DuPont PDS 1000He Biolistic gun. Transgenic shoots were selected on RMOP medium containing 500 µg/ml spectinomycin dihydrocloride. Putative primary transformants were identified by histochemical staining for β-glucuronidase activity encoded by uidA (Jefferson, In Genetic Engineering, Vol. 10, Settlow, J. K., ed. Plenum Press, NY & London, pp 247–263, 1988). A uniform population of transformed plastid genomes was verified by Southern analysis (data not shown).

Primer Extension Analysis to Map RNA 5'-ends.

Total leaf RNA was isolated from leaves of in vitro grown plants by the method of Stiekema et al., supra. Primer extension reactions were carried out on 20 µg of RNA with primer uidA PE1 as described by Allison and Maliga (1995) using primer P3: 5'-GGCCGTCGAGTTTT TTGATTTCACGGGTTGGGG-3' (SEQ ID NO:52) (which is complementary to the uidA coding region.

DNA Sequence Analysis. DNA sequence analysis was carried out utilizing the Wisconsin Sequence Analysis Package (Genetics Computer Group, Inc.) as described in Example IV.

Results and Discussion

Figure 6:
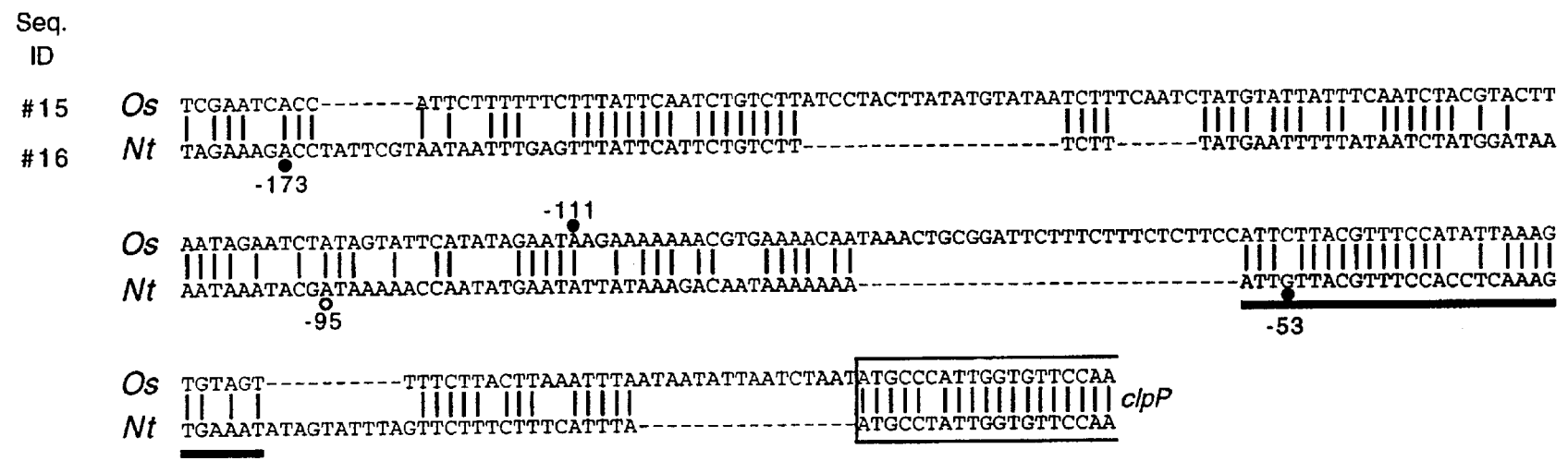
Figure 7:
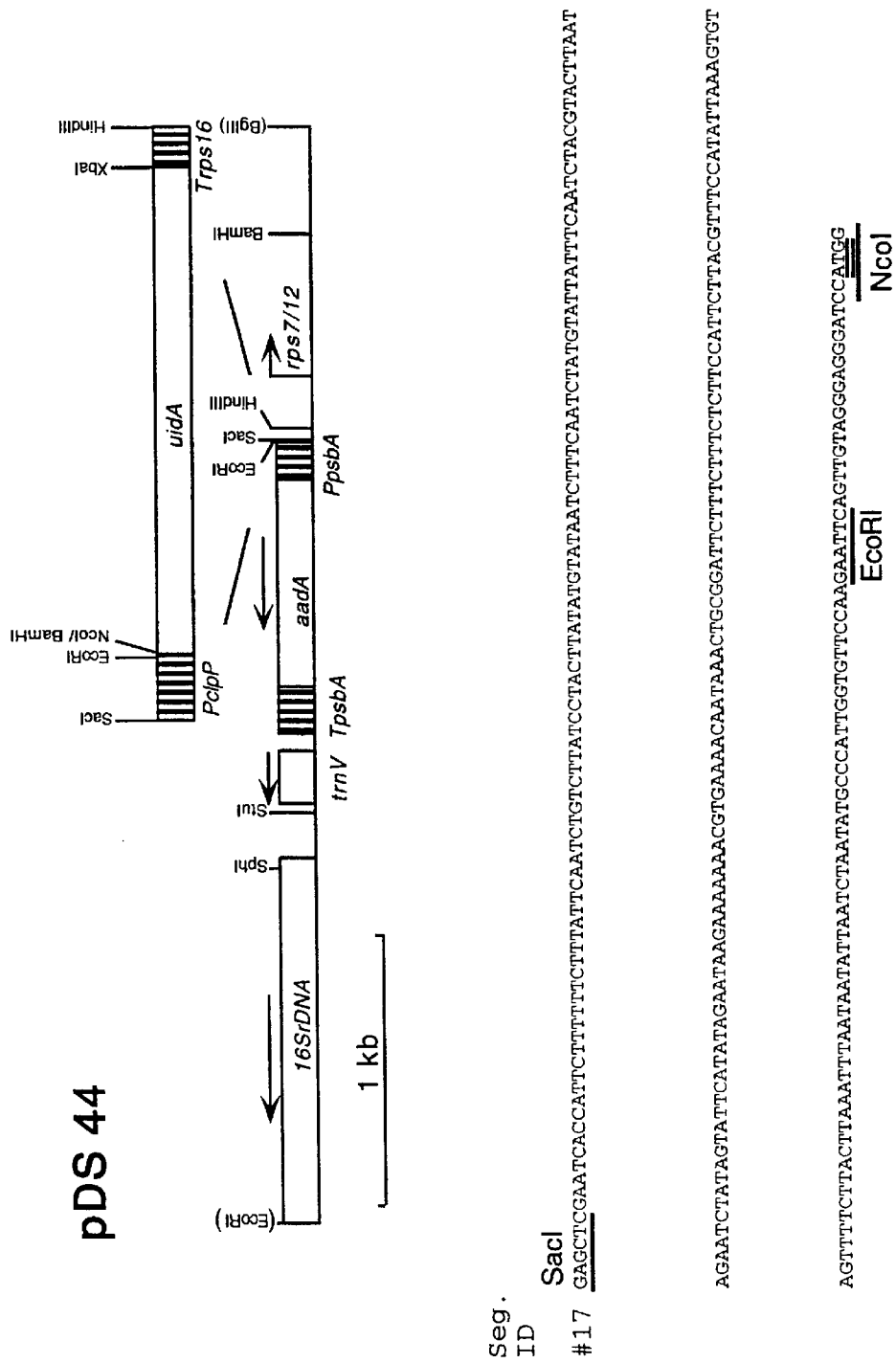
FIG. 7 is a schematic drawing of the plastid targeting region of plasmid pDS44. On top is shown the restriction map of the chimeric uidA gene. PclpP is the rice clpP promoter fragment between the SacI and Nco site (SEQ ID NO: 17) which is shown at the bottom of FIG. 5. uidA encodes the β-glucuronidase reporter enzyme. Trps16 is the rps16 ribosomal protein gene 3' untranslated region. A map of the transforming DNA in a pPRV111A plastid vector (Gene Bank Accession No. U12812) is also shown (Zoubenko et al., Nucleic Acids Res. 22:3819–3824, 1994).

Construction of Transgenic Plants. The sequence of rice clpP upstream region included as a promoter fragment in plasmid pDS44 is shown in FIG. 6. In rice, this region contains the Os-PclpP-111 Type I NEP promoter. The cognate sequence in tobacco contains two NEP promoters and one PEP promoter. The Os-PclpP-111 NEP promoter was cloned upstream of a uidA coding region (encoding β-glucuronidase or GUS) with a ribosome binding site, and the rps16 3'-untranslated region (Trps16) for stabilization of the mRNA shown in FIG. 7. The chimeric uidA gene was cloned next to a selectable spectinomcyin resistance (aadA) gene in the pPRV111A plastid vector, Genebank Accession No. U12812, and introduced into tobacco plastids. A schematic drawing of the vector is shown in FIG. 7. Plastid transformants were selected on spectinomycin medium. Out of 25 spectinomcyin resistant lines, 12 were GUS positive. Integration of uidA at the target site was confirmed by Southern analysis (data not shown).

Figure 8A:
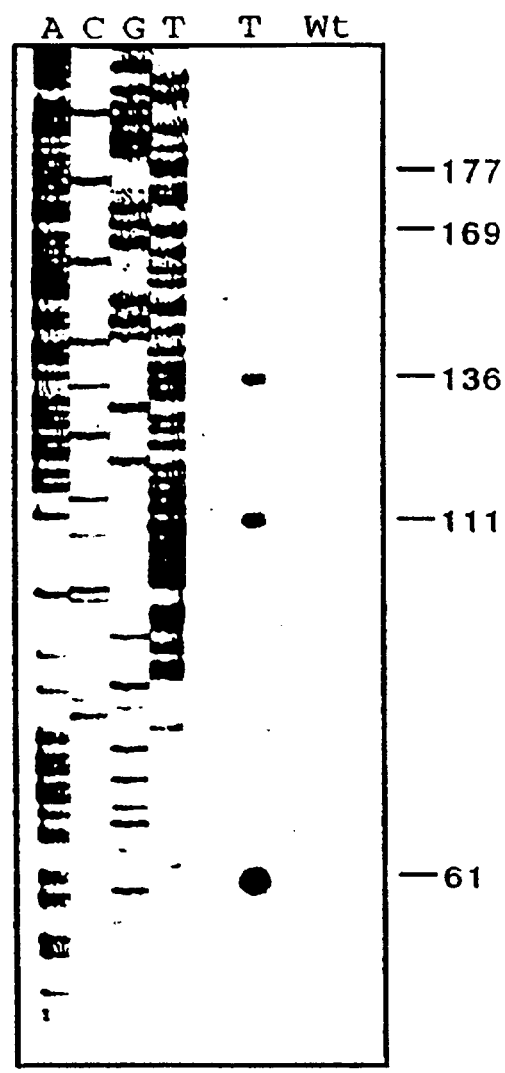
FIGS. 8A and 8B illustrate the promoter activity of the rice clpP promoter region in transgenic tobacco plastids.

Primer extension analysis to test promoter activity. Primer extension analysis was carried out to map uidA 5'-ends initiating in the Os-PclpP-111 promoter region. Three major and two minor uidA transcripts were identified in the leaves of transgenic plants (FIG. 8A). A major transcript 5' end mapped to nucleotide position −111, the same position as in rice. This result indicates that the rice Type I PclpP-111 promoter is properly recognized in tobacco, a dicot, indicating the broad applicability of this promoter in a variety of plant species. The second major transcript with the most intense signal was found at the rice −61 position. This transcript 5'-end mapped to a rice sequence with a 29 nucleotide stretch of homology to the tobacco Nt-PclpP-53 promoter region (FIG. 6). This was unexpected, since this region in rice and maize is transcriptionally silent (Example I). The third major transcript mapped to position −136 which falls within the upstream monocot NEP box (Example I).

Figure 8B:
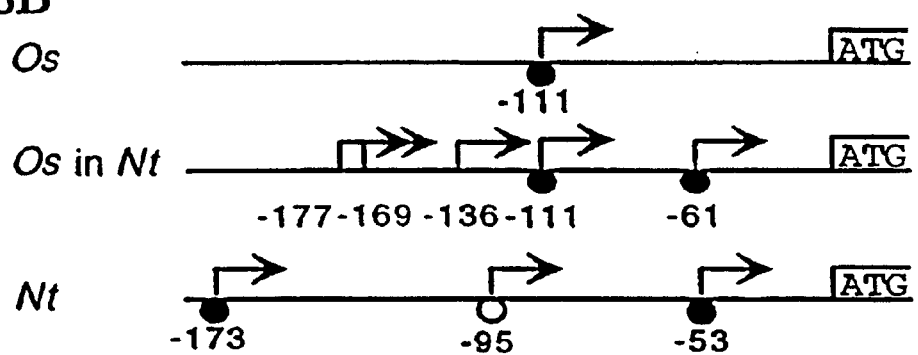

The two minor transcript 5'-ends mapped to nucleotide positions −169 and −177 (FIG. 8). These transcripts are absent in rice leaf RNA, and they do not correspond to any of the known tobacco clpP transcripts. Therefore, these 5'-ends may be primary transcripts of fortuitous PEP or NEP promoters, or are processed mRNA 5'-ends.

Sequence alignment of the regions containing the clpP promoters The rice clpP promoter fragment was transcriptionally active in tobacco. This promoter sequence corresponds to the tobacco Type II PclpP-53 promoter. In this region, rice and tobacco share a 29 nucleotide stretch of homologous sequence with 23 conserved nucleotides. To test the conservation of this same region during evolution, sequences around the clpP transcription initiation sites were aligned, including those of the liverwort Marchantia polymorpha (Kohchi et al., *Curr. Genet.* 14:147–154, 1988), the conifer Pinus contorta, (Clarke et al., *Plant Mol. Biol.* 26:851–862, 1994), dicots tobacco (Hajdukiewicz et al., 1997, supra) spinach, Arabidopsis (Westhoff, *Mol. Gen. Genet.* 201:115–123, 1985) and the monocots maize and rice. See FIG. 9. With the exception of tobacco, a single transcription initiation site was mapped for each of the clpP genes. We have found, that the 29-nucleotide segment around the clpP transcription initiation site is conserved, (underlining) suggesting that clpP is transcribed by NEP in all of these species.

The data presented in this Example show that the rice Os-PclpP-111 NEP promoter is properly recognized in tobacco plastids. Transcription from the rice PclpP-111 NEP promoter in tobacco was observed presumably because the region around the transcription initiation site includes the dicot Type I NEP promoter consensus. As in rice, the Os-PclpP-111 NEP promoter is active in mature tobacco leaves. Therefore, it belongs to the relatively small number of Type I NEP promoters which are active in mature chloroplasts as well as proplastids.

Transcription from the rice clpP 5' region at a second site, with a short stretch of homologous sequence to the tobacco PclpP-53 Type II NEP promoter was unexpected. Since rice contains all the cis elements required for Type II promoter activity, lack of transcription in rice should be due to the evolutionary loss of the specificity factor required for Type II promoter recognition. This specificity factor is well conserved during evolution, as evidenced by an active Type II clpP promoter in the liverwort Marchantia polymorpha and the conifer Pinus contorta (FIG. 9).

Experiments reported here for the rice Os-PclpP-111 NEP promoter suggest that the Type I NEP transcription machinery is sufficiently conserved between monocots and dicots to ensure faithful recognition of heterologous promoters. The clpP mRNA accumulates to significant levels in all plastid types (Shanklin et al., 1995, supra; Hajdukiewicz et al., 1997, supra; Example I). Therefore, the strong, constitutive Os-PclpP-111 NEP promoter is suitable for the expression of chimeric genes in a broad range of crops.

EXAMPLE III
In vivo Definition of a Type II Promoter, PclpP-53, for the Nuclear Encoded Plastid RNA Polymerase (NEP)

In tobacco the clpP gene is transcribed from three major NEP promoters initiating transcription −511, −173 and −53 nucleotides upstream of the translation initiation codon, and from a PEP promoter (5' end at −95). Transcription from the Type II PclpP-53 NEP promoter is maintained in the green leaves of wild-type tobacco plants. Therefore, given its potential to drive the expression of selectable marker genes, the constitutive PclpP-53 promoter was chosen for analysis.

Materials and Methods for Example III

Figure 10:
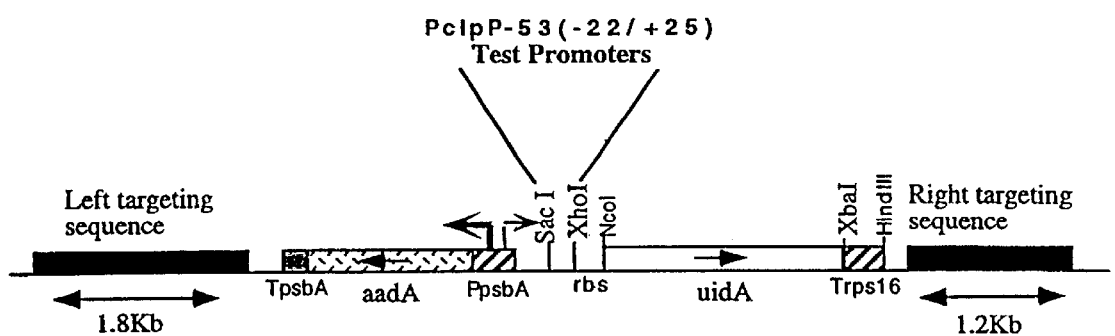
FIG. 10 shows the plastid targeting region of plasmid pPS18. Plasmid pPS18 has the plastid targeting region of plastid vector pPRV111A, GenBank Accession No: U12812, with a chimeric uidA gene expressed from the PclpP-53(−22/+25) promoter. DNA sequence of the uidA gene is shown in FIG. 13 (SEQ ID NO: 27).

Construction of Plasmids. Plasmid pPS8 contains a uidA reporter gene as a SacI-HindIII fragment in a pBSKS+ plasmid (Stratagene). The chimeric uidA gene consists of: Between the SacI and XhoI sites, the PclpP-53(−22/+25) promoter fragment containing 22 nt upstream and 25 nt downstream (+1 is nt where transcription initiates) of the clpP transcription initiation site; Between XhoI and NcoI sites, a ribosome binding site; Between the NcoI and XbaI sites, the uidA coding region with an N-terminal c-myc tag corresponding to amino acids 410–419 (EQKLISEEDL; SEQ ID NO: 53) within the carboxy terminal domain of the human c-myc protein (Kolodziej and Young, *Meth. Enz.* 194:508–519, 1991); Between the XbaI and HindIII sites the 3' untranslated region of the rps16 ribosomal protein gene (Trps16). DNA sequence of the chimeric uidA gene between the SacI and HindIII sites in plasmid pPS18 is shown in FIG. 13. Relevant restriction sites of the chimeric uidA gene are shown in FIG. 10, where the uidA gene is shown as part of plasmid pPS18. Plasmid pPS18 was obtained by cloning the uidA gene as a SacI-HindIII fragment into SacI-HindIII-digested pPRV111A plastid transformation vector. Plasmid pPRV111A, a pBSKS+plasmid derivative (Strategene), and was described in Zoubenko et al., 1994, supra.

Figure 11:
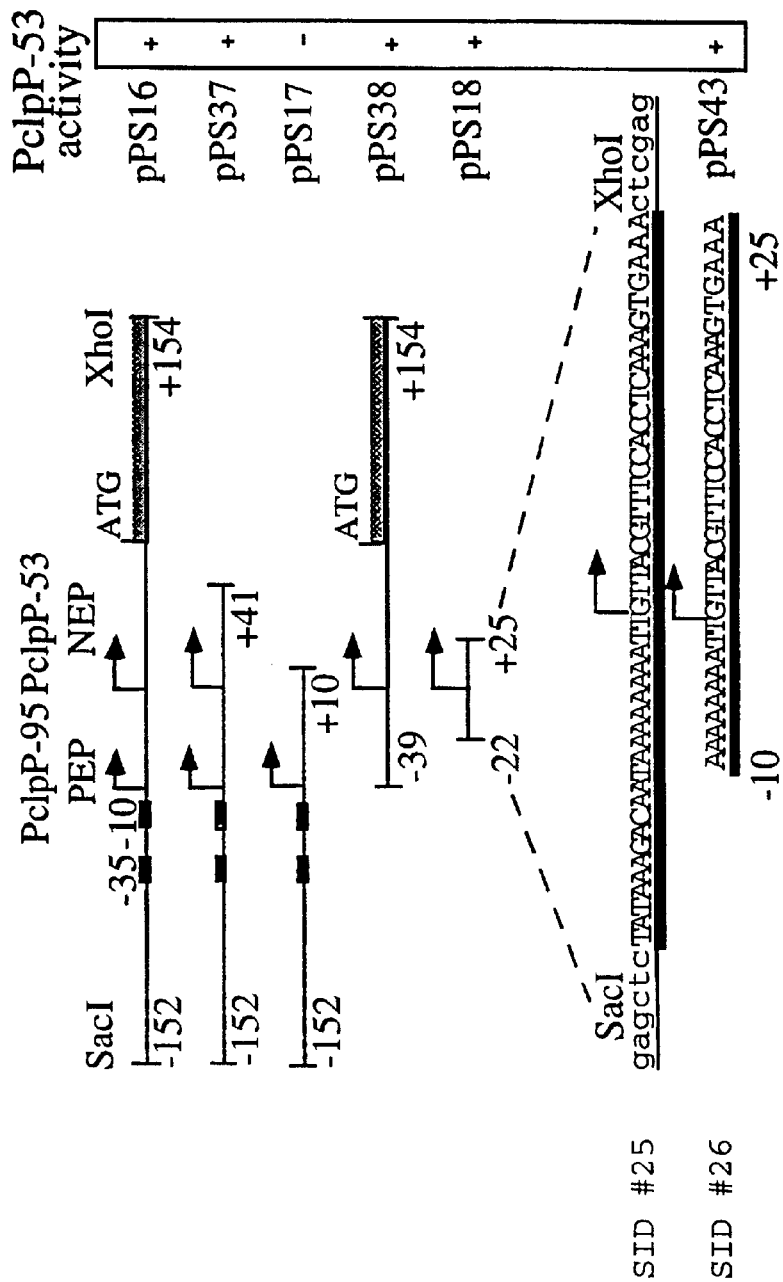
FIG. 11 depicts the clpP 5' fragments tested for promoter activity. The largest segment contains the PclpP-53 and PclpP-95 transcription initiation sites derived from Type II NEP and PEP promoters, respectively. The boundaries give the distance in nucleotides from PclpP-53 transcription initiation site (+1). SEQ ID NO: 25 contains the sequences present between −22 and +25 and SEQ ID NO: 26 shows the nucleotides present between −10 and +25. Both sequences function as promoters.

Plasmids pPS16, pPS37, pPS17 and pPS38 listed in FIG. 11 were obtained from plasmid pPS18 by replacing the PclpP-53(−22/+25) SacI-XhoI promoter fragment with the PclpP-53(−152/+154), PclpP-53(−152/+41), PclpP-53(−152/+10), PclpP-53(−39/+154) promoters, respectively. The SacI-XhoI fragments were obtained by PCR amplification. PCR primers are listed according to the position of the terminal nucleotide relative to the transcription initiation site (it is the complement of nt 74557 in the tobacco plastid genome: accession no. Z00044):

```
clpP-152  ccgagctcGAATGAGTccATACTTAT     SEQ ID NO: 54 clpP-39   ccgagctcAAAACcAATATGAATATTATA  SEQ ID NO: 55 clpP -22  ccgagctcTATAAAGACAATAAAAAAAAT  SEQ ID NO: 56 clpP30    ccctcgaGAAACGTAACAATTTTTTTT    SEQ ID NO: 57
10 clpP30    ccctcgagTTTCACTTTGAGGTGGA      SEQ ID NO: 58
25 clpP30    ccctcgagAGAACTAAATACTATATTTC   SEQ ID NO: 59
41 clpP30    ccctcgagATATGACCCAATATATCTG    SEQ ID NO: 60
154
``` genome are in capital letters; added nucleotides to create restriction sites (underlined) are in lower case letters.

Tobacco Plastid Transformation. Plastid transformation and regeneration of tobacco plants was carried out as described by Svab and Maliga, 1993, supra. Transgenic plants were selected on regeneration medium containing 500 µg/ml spectinomycin dihydrochloride.

Primer Extension Analysis. Total leaf RNA was isolated from the leaves of transgenic plants maintained on RM medium, by the method of Stiekema et al.,1988, supra. Primer extension reactions were carried out as described by Allison and Maliga, 1995, supra, using 15 µg of the total RNA and primer PE1 complimentary to the 5' end of the uidA coding sequence. Primer PE1 sequence: 5'-GGCCGTCGAGTTTTTTGATTTCACGGGTTGGGG-3' (SEQ ID NO: 61)

Results and Discussion

To identify functionally important sequences in the Type II PclpP-53 promoter, expression of reporter genes driven by sequences surrounding the clpP-53 NEP transcription initiation site was measured. Deletion of sequences from the 5' and 3' ends facilitated the determination of the boundaries of the promoter. These studies revealed that a 47-bp fragment is sufficient to support accurate transcription initiation. The data further suggest that not more than 28 bp out of 47 are essential for promoter function. A majority of the relevant sequences are downstream of the transcription initiation site.

Since all plastid promoters are within about 150 nucleotides of the transcription initiation site, transcription initiation in vivo from a 306-bp fragment (−152/+154) surrounding the clpP-53 transcription initiation site was assessed. For testing promoter function, clpP fragments were cloned upstream of a uidA reporter construct encoding β-glucuronidase. See FIG. 11. The uidA construct has a ribosome binding site between the XhoI and NcoI restriction sites, as well as the 3'-untranslated region of the plastid rps16 gene (Trps16) for stabilization of the mRNA. The chimeric uidA gene was introduced into tobacco plastids by linkage to a selectable spectinomycin resistance (aadA) gene. The 306-bp fragment contains a PEP and a NEP promoter (FIG. 11). Functioning of both promoters was established by primer extension analysis. See FIG. 12.

Figure 12:
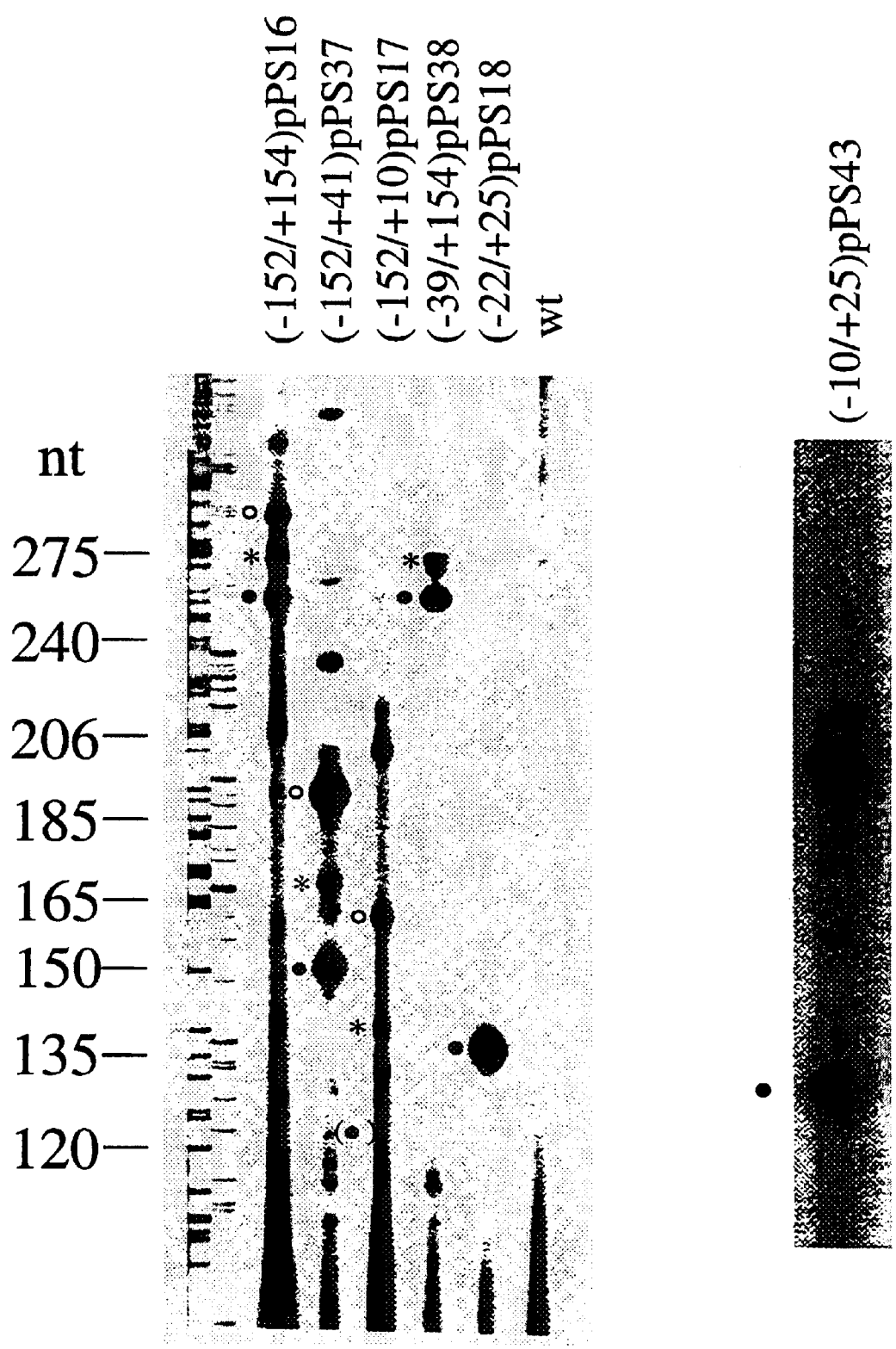
FIG. 12 depicts the results of primer extension analysis to test promoter activity of clpP 5' fragments included in FIG. 11. Transcripts derived from PclpP-53 (−53), a minor NEP promoter (*), PclpP-95 (−95) and PclpP-173 (−173) are marked. DNA sequences on the side give distance from primer in nucleotides.

After confirming that the 306-bp fragment is sufficient to drive NEP transcription, a series of deletions were made from the 5' as well as 3' end. These constructs were then tested for transcription initiation in vivo in tobacco. The schematic design of the promoter deletions is shown in FIG. 11, the primer extension data are shown in FIG. 12. Primer extension analysis on the series of deletions showed that sequences extending from −10 to +25 (pPS43; FIG. 12) and −5 to +25 (pPS44; not shown) are sufficient to support accurate initiation from clpP-53. Upon overexposure, a faint band or the proper size is observed even in the +1 to +25 construct (pPS45, not shown). Also, transcription from the NEP promoter was abolished completely in the −152/+10 construct, (pPS17; FIG. 12) and in the −22 to +21 construct, (pPS41; not shown). This indicates that sequences between +5 and +25 are important for transcription from the NEP promoter. Some of this data is summarized in FIGS. 11 and 12.

Sequences required for transcription by the NEP polymerase are not known. Based on conservation of the ATAGAATA/GAA (SEQ ID NO:64) around the transcription initiation site, Hajdukiewicz et al., 1997, supra, most NEP promoters were classified as Type I. The promoter studied here, PclpP-53, lacks this sequence motif, because of which it is classified as Type II. Transcription analysis in the truncated promoter fragment of plasmid pPS18 in vivo shows that sequences required to support transcription from PclpP-53 are located within a 30 basepair fragment extending from −5 to +25 with respect to the transcription initiation site. Furthermore, nucleotides between +10 and +25 are important for transcription initiation, since there is no transcription from clpP promoter derivatives in plasmid pPS17 and pPS41 lacking this region.

Expression of the rice clpP promoter region revealed a transcript that mapped to a region with homology to the transcription initiation site of the PclpP-53 promoter. Alignment of the rice and the tobacco sequences show significant homology downstream of the transcription initiation site, and not much homology upstream. Considering that this rice sequence was recognized by tobacco in vivo (Example II), sequences that are important for transcription initiation should be present in the rice sequence. Combining this information with the finding that −22/+25 sequences are sufficient for transcription initiation in vivo, it appears that sequences 5'-ATTGTTACGTTTCCACCTCAAAGTGAAA-3' (portion of SEQ ID NO: 25) extending from −3 to +25 contain the information which is important for PclpP-53 promoter function.

Since the constitutive Type II PclpP-53 is efficiently transcribed in all tissue types, it is useful for the expression of selectable marker genes, and of proteins of economic value in all dicot plants.

EXAMPLE IV

Plastid Promoter Utilization in Rice Embryogenic Cell Culture

The utilization of the clpP promoter in tobacco and maize plastids is described in the previous examples. The present example is directed to the analysis of plastid promoter utilization in rice. The 5' ends of several mRNA species were mapped in samples derived from cultured embryogenic rice cells and leaves. The RNAs for clpP and 16SrRNA are relatively abundant in embryogenic rice cells indicating that the promoters of these genes may be used to advantage to drive plastid expression of selectable marker genes and/or foreign genes of interest in rice.

Plastid transformation in rice is highly desirable. The present example provides compositions and methods to effectuate rice plastid transformation in embryogenic cultured rice cells. Such cells may be efficiently regenerated into mature plants (Vasil, I K (1994) Plant Mol Biol 25:925–937; Christou, P (1996) Trends Plant Sci 1:423–431). Data from cultured tobacco (BY2) cells suggest that plastid promoter utilization in tissue culture may be different from those in leaves (Vera A, Sugiura M (1995) Curr Genet 27:280–284; Vera A, Hirose T, Sugiura M (1996) Mol Gen Genet 251:518–525 et al., 1996; Kapoor S, Suzuki J Y, Sugiura M (1997) Plant J 11:327–337). The data presented herein reveal that cultured embryogenic rice cells and leaves utilize the same promoter. rbcL, atpB, 16SrDNA and clpP have only one promoter each which is recognized by the plastid-encoded plastid RNA polymerase (PEP). In contrast, clpP is transcribed by the nucleus-encoded plastid RNA polymerase (NEP) in both samples. The RNAs for clpP and 16SrRNA are relatively abundant in embryogenic cells indicating that the promoters of these genes may be suitable to drive the expression of selectable marker genes.

Materials and Methods for Example IV

Plant Materials. Embryogenic rice callus was initiated from mature seed of cv. Taipei 309 on LS2.5 medium (Abdullah R, Cocking E C, Thompson J A (1986) Bio/Technology 4:1088–1090). The calli were introduced into liquid AA medium (Muller A J, Grafe R (1978) Mol Gen Genet 161: 67–76) to establish embryogenic suspension cultures, and subcultured at biweekly intervals. DNA and RNA were prepared from 3 month old cultures 14 days after subculture. Plants were regenerated from embryogenic calli on complete MS medium supplemented with 2 mg/L BAP and 3% sucrose (Murashige T, Skoog F (1962) Physiol Plant 15: 473–497 1962) and transferred onto hormone-free MS medium. Leaves for the isolation of nucleic acids were taken from these plants after four months.

RNA and DNA gel blots. Total cellular RNA was prepared according to Stiekema et al., 1988, supra. The RNA (5 μg per lane) was subjected to electrophoresis in a formaldehyde-agarose gel, blotted and hybridized (Hajdukiewicz P T J, Allison L A, Maliga P (1997) EMBO J 16:4041–4048). Double-stranded ptDNA probes were prepared by random-primed $^{32}$P-labeling of PCR-generated or gel-purified DNA fragments. The sequence of the primers used for PCR, along with their positions within the tobacco (N.t.; accession no. Z00044; Shinozaki et al. 1986, supra) or maize (Z.m.; accession no. X86563; Maier et al. 1995, supra) ptDNA are as follows:

Primer extension reactions were carried out with 1 μg of RNA from leaves, and 10 μg (clpP, 16SrDNA) and 30 μg (rbcL, atpB) of RNA from embryogenic cells.

Results and Discussion

Several plastid promoters have been identified in rice and related monocots. To assess whether these promoters would be suitable to drive expression of selectable marker genes and/or foreign genes of interest in these plant species, transcript accumulation was examined. The rbcL gene in rice and maize is transcribed from a PEP promoter (Mullet et al., 1985, supra; Nishiziwa Y, Hirai A (1987) Jpn J Genet 62:389–395). The atpB gene in maize chloroplasts is transcribed from a PEP promoter (Mullet et al., 1985, supra), whereas in maternal white iojap seedlings lacking PEP it is transcribed from an alternative NEP promoter. The 16SrDNA gene (the first gene of the plastid ribosomal RNA operon) in barley chloroplasts is transcribed from a PEP promoter (Reinbothe S, Reibothe C, Heintzen C, Seidenbecher C, Parthier B (1993) EMBO J 12:1505–1512), whereas in the white albostrians seedlings lacking PEP it is transcribed from an uncharacterized NEP promoter (Hess et al., 1993, supra). The clpP gene in wild-type and iojap maize chloroplasts is transcribed from a NEP promoter.

| Gene | 5' nt position in plastid DNA | Sequence | SEQ ID NO: |
|---|---|---|---|
| atpB (Z.m.) | 55860 (C) | GAGAGGAATGGAAGTGATTGACA | (62) |
|  | 55103 | GAGCAGGGTCGGTCAAATC | (63) |
| clpP (Z.m.) | 69840 | ATCCTAGCGTGAGGGAATGCTA | (64) |
|  | 70064 (C) | AGGTCTGATGGTATATCTCAGTAT | (65) |

The following ptDNA fragments were used as probes: rbcL (N.t.), a BamHI fragment (nucleotides 58047 to 59285 in ptDNA); 16SrDNA (N.t.), EcoRI to EcoRV fragment (nucleotides 138447 to 140855).

The probe for tobacco 25S rRNA was from plasmid pKDR1 (Dempsey et al., 1993, supra) containing a 3.75 kb EcoRI fragment from a tobacco 25S/18S locus cloned in plasmid pBR325.

Total leaf DNA for relative plastid genome copy number determination was prepared (Mettler I J (1987) Plant Mol Biol Rep 5:346–349), digested with the EcoRI restriction endonuclease, separated on 0.7% agarose gels, blotted and hybridized with the plastid 16SrDNA and cytoplasmic 25SrDNA probes (Allison et al., 1996, supra).

Primer extension analysis. Primer extension reactions were carried out on total leaf RNA as described (Allison and Maliga, 1995, supra). The primers are listed below, with nucleotide position in the published rice plastid genome sequence (Hiratsuka et al., 1989, supra).

Figure 14:
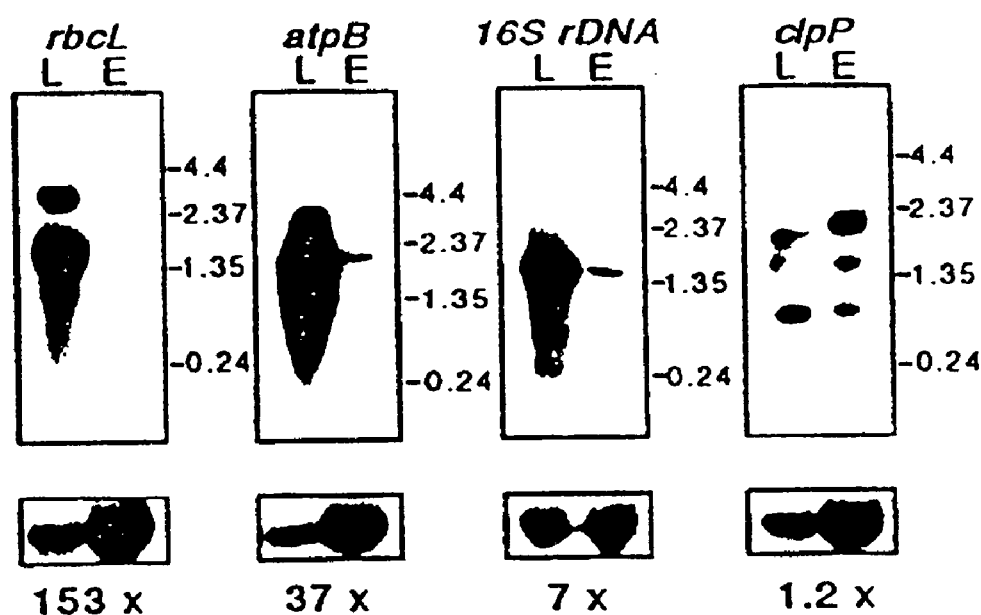
FIG. 14 is a northern blot showing RNA steady state concentrations in leaf (L) and in embryogenic cultured cells (E) of rice. To control for loading, the blots were stripped and probed for cytoplasmic 25S ribosomal RNA (lower panels). Hybridization signals were quantified with a Molecular Dynamics PhosphorImager. The fold excesses in leaves over cultured cell signals are shown below the panels.
Figure 15:
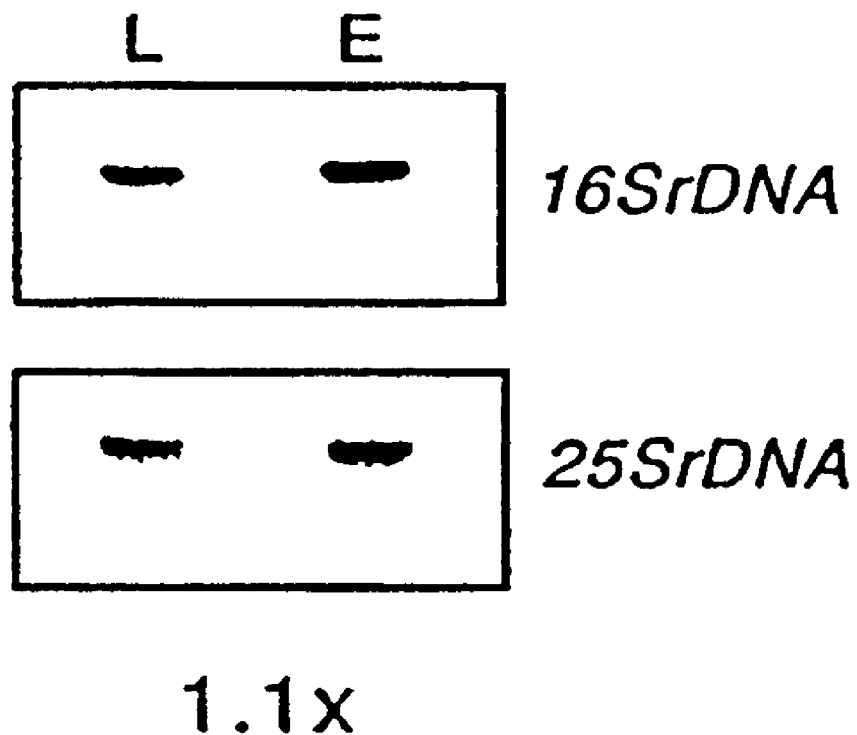
FIG. 15 is a Southern blot showing the relative plastid genome copy number in leaves (L) and in cultured embryogenic cells (E) of rice. EcoRI-digested total cellular DNA (approximately 2 µg per lane) was probed for plastid 16SrDNA (upper) and nuclear-encoded 25SrDNA (lower). Hybridization signals were quantified with a Molecular Dynamics PhosphorImager. The ratio of 16SrDNA/25SrDNA signal intensity in leaves relative to embryogenic cells was 1.1.

To determine the level of expression of these genes in embryogenic rice cells and leaf cells, accumulation of mRNAs was assessed on Northern blots. The data reveal that transcript levels in embryogenic cells relative to leaves were barely detectable for rbcL (153-times lower), reduced for atpB (37-fold lower) and 16SrDNA (7-fold lower), and similar for clpP (approximately 1.1-times lower). See FIG. 14. Interestingly, the number of plastid genome copies (ptDNA) per cell is about the same in embryogenic cells and leaves. See FIG. 15. Accordingly, the differences in transcript levels represent values normalized for ptDNA copy number.

To further characterize active plastid promoters, transcript 5' ends were mapped by primer extension in cultured embryogenic cells and in leaves. Two different 5' ends, at 312 and 58 nucleotides upstream of the translation initiation codon, were mapped for rbcL. See FIG. 16. The same two 5'-ends were identified in leaf chloroplasts, and in the plastids of embryogenic cells. Two 5'-ends were mapped to similar positions by S1 nuclease analysis in rice chloroplasts

| Gene | 5' nt position in plastid DNA | Sequence | SEQ ID NO: |
|---|---|---|---|
| rbcL | 54124 (C) | ACTTGCTTTAGTTTCTGTTTGTGGTGACAT | (66) |
| atpB | 53287 | AGAAGTAGTAGGATTGGTTCTCATAAT | (67) |
| 16S rRNA | 123777 | CCGCCAGCGTTCATCCTGAGC | (68) |
| clpP | 68263 | GGTACTTTTGGAACACCAATGGGCAT | (69) |

(Nishizawa and Hirai, 1987, supra). The rbcL −312-end is downstream of −10/−35 $\sigma^{70}$-type promoter elements which are conserved in monocots; the −58-end is generated by RNA processing (Mullet et al., 1985, supra; Reinbothe et al., 1993, supra).

For atpB, a single 5'-end was mapped 310 nucleotides upstream of the translation initiation codon. As for rbcL, the same 5'-ends were identified in embryogenic cells and leaves. See FIG. 16. The −310 end is associated with PEP promoter elements, and has been reported earlier in chloroplasts for rice (Nishizawa Y, Hirai A (1989) Jpn J Genet 64:223–229) and maize (Mullet et al., 1985, supra).

Figure 16:
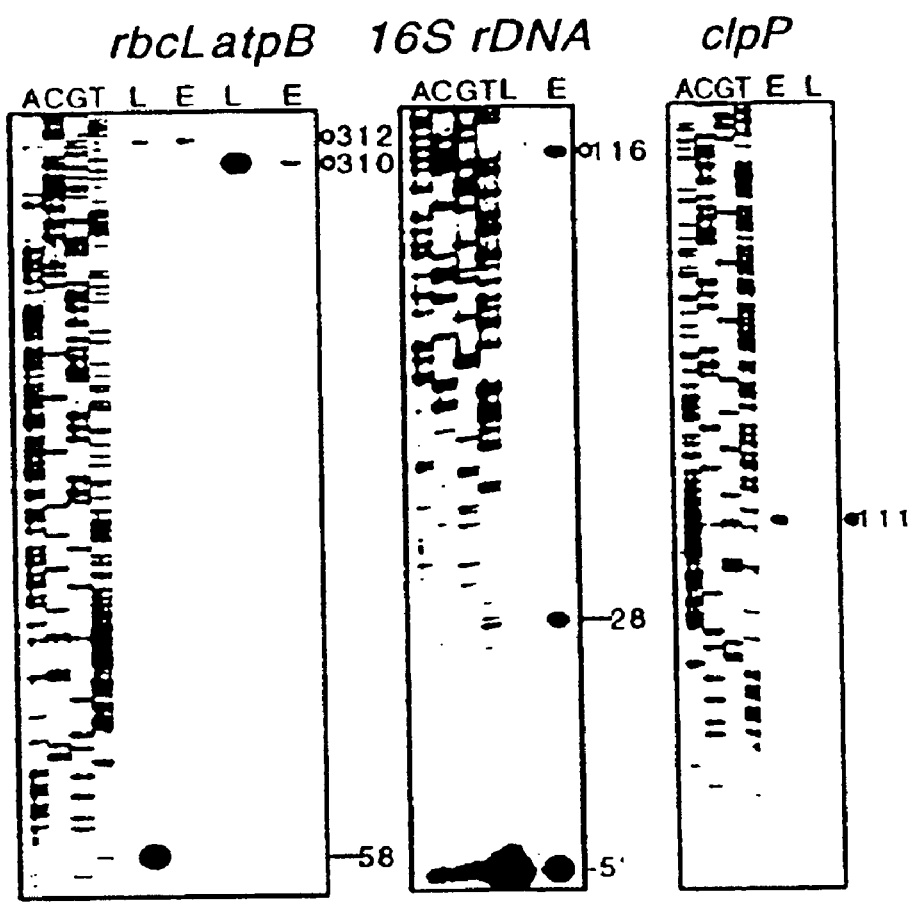
FIG. 16 is an autoradiograph depicting the mapping results of plastid mRNA promoters in rice leaves (L) and embryogenic cultured cells (E) using primer extension analysis. Numbers on the right indicate the distance between the translation initiation codon (ATG) and 5' ends of primary transcripts (PEP, ○; NEP, ●), or of processed mRNAs (−). DNA sequences on the left are size markers. Sequence ladders shown for 16S rDNA and clpP were obtained with homologous template and oligonucleotides used for primer extension analysis.

For the rRNA operon, the same two 5' ends were mapped upstream of the mature 16SrRNA in embryogenic cells and in leaves shown in FIG. 16. Based on DNA sequence conservation, the −116 end is the product of a PEP promoter whereas the −28 end derives from RNA processing. See FIG. 17A; Strittmatter G, Godzicka-Josefiak A, Kossel H (1985) EMBO J 4:599–604; Vera and Sugiura, 1995, supra; Allison et al., 1996, supra).

For clpP, the same 5' end was mapped in embryogenic tissue culture cells and in leaves. See FIG. 16. The transcript initiates 111 nucleotides upstream of the translation initiation codon within the 10-nucleotide NEP consensus, shown in FIG. 5A, and is the product of the clpP Type-I NEP promoter.

Mapping of RNA 5 ends upstream of rbcL, atpB, 16SrDNA and clpP identified the same promoters in cultured embryogenic cells and in the leaves of rice. The data obtained from these studies in rice can be contrasted with the results reported for tobacco. In tobacco, atpB and 16SrDNA are preferentially transcribed from PEP promoters in leaves, and from NEP promoters in BY2 tissue culture cells (Vera and Sugiura 1995; Kapoor et al. 1997). In rice embryogenic cultures, no PEP to NEP promoter switch was observed for any of the plastid genes examined. The data suggest that a PEP to NEP promoter switch is not essential for adaptation to cell culture. Alternatively, atpB and 16SrDNA, genes which have PEP and NEP promoters in other monocots as discussed in the previous examples, have no NEP promoters in rice.

One important difference between embryogenic rice cells and the tobacco BY2 cell line is the length of time in culture. The rice cell culture line described herein is only a few month old and has maintained the ability to regenerate plants. The BY2 cell line has been grown in culture for several years and has lost the capacity for plant regeneration (Yasuda T, Kuroiwa T, Nagata T (1988) Planta 174:235–241). Accordingly the possibility remains that in BY2 cells plastid gene expression may be different from tobacco cells in a short-term culture or in a tobacco plant.

The results presented herein provide practical implications for the production of transgenic rice cells and or plants. Two powerful promoters are described herein which are active in rice embryogenic cells: the clpP NEP promoter and the rrn PEP promoter. Both promoters are suitable to drive the expression of selectable marker genes for plastid transformation in embryogenic rice cells.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated clpP promoter element for producing at least one exogenous protein of interest in plastids of plant cells, wherein said clpP promoter element is selected from the group consisting of SEQ ID NO:3, SEQ ID NO:12 and SEQ ID NO:30.

2. An isolated clpP promoter element for producing at least one exogenous protein of interest in plastids of a dicot, wherein said clpP promoter element is SEQ ID NO:23.

3. An isolated clpP promoter element of claim 2, wherein said dicot is tobacco.

* * * * *